United States Patent
Rao et al.

(10) Patent No.: US 11,728,031 B2
(45) Date of Patent: Aug. 15, 2023

(54) SOFTWARE APPLICATION FOR PATIENT CARE AND RELATED DEVICE, SYSTEM, AND METHOD

(71) Applicant: BFC MED LLC, Tucson, AZ (US)

(72) Inventors: Arun Rao, Tucson, AZ (US); Lacey Rao, Tucson, AZ (US)

(73) Assignee: BFC MED LLC, Tucson, AZ (US)

( * ) Notice: Subject to any disclaimer, the term of this patent is extended or adjusted under 35 U.S.C. 154(b) by 730 days.

(21) Appl. No.: 16/601,322

(22) Filed: Oct. 14, 2019

(65) Prior Publication Data
US 2020/0118680 A1 Apr. 16, 2020

Related U.S. Application Data

(60) Provisional application No. 62/745,242, filed on Oct. 12, 2018.

(51) Int. Cl.
| | | |
|---|---|---|
| *G16H 40/67* | (2018.01) | |
| *G16H 10/60* | (2018.01) | |
| *G16H 40/40* | (2018.01) | |
| *G16H 40/20* | (2018.01) | |
| *G16H 80/00* | (2018.01) | |

(52) U.S. Cl.
CPC .............. *G16H 40/67* (2018.01); *G16H 10/60* (2018.01); *G16H 40/20* (2018.01); *G16H 40/40* (2018.01); *G16H 80/00* (2018.01)

(58) Field of Classification Search
CPC ........ G16H 10/60; G16H 15/00; G16H 40/20; G16H 80/00; G06F 3/0482; G06F 3/04817; A61B 5/7435
See application file for complete search history.

(56) References Cited

U.S. PATENT DOCUMENTS

| | | | |
|---|---|---|---|
| 9,020,476 B2 | 4/2015 | Leipzig et al. | |
| 9,811,633 B2 | 11/2017 | Cronrath et al. | |
| 2010/0198614 A1 | 8/2010 | Chopra et al. | |
| 2011/0010087 A1 | 1/2011 | Wons et al. | |
| 2012/0101847 A1* | 4/2012 | Johnson | G16H 10/60 705/2 |
| 2013/0124226 A1 | 5/2013 | Gedala | |
| 2013/0304511 A1 | 11/2013 | Gunter | |

(Continued)

OTHER PUBLICATIONS

Gordon CR, Rezzadeh KS, Li A, et al. Digital mobile technology facilitates HIPAA-sensitive perioperative messaging, improves physician-patient communication, and streamlines patient care. Patient Saf Surg. 2015;9:21. Published May 23, 2015. doi:10.1186/s13037-015-0070-9 (Year: 2015).*

(Continued)

*Primary Examiner* — Joseph D Burgess
(74) *Attorney, Agent, or Firm* — Volpe Koenig

(57) ABSTRACT

In an embodiment, an electronic device includes a display screen, a memory circuit, and computing circuitry, which is coupled to the display screen and to the memory circuit, and which is configured to cause the display screen to display icons that are each related to respective data regarding a patient at a medical facility, to retrieve, from the memory, the respective data in response to a user of the electronic device selecting, via the display screen, a corresponding one of the displayed icons, and to cause the display screen to display the retrieved respective data.

37 Claims, 44 Drawing Sheets

(56) References Cited

U.S. PATENT DOCUMENTS

| | | | |
|---|---|---|---|
| 2014/0249844 | A1 | 9/2014 | Liberty et al. |
| 2015/0127359 | A1 | 5/2015 | Iravani |
| 2015/0213202 | A1 | 7/2015 | Amarasingham et al. |
| 2015/0310659 | A1 | 10/2015 | Spear et al. |
| 2015/0332020 | A1 | 11/2015 | Lo et al. |
| 2016/0042133 | A1 | 2/2016 | Sidel |
| 2016/0147951 | A1 | 5/2016 | Francois et al. |
| 2017/0116384 | A1 | 4/2017 | Ghani |
| 2017/0262604 | A1 | 9/2017 | Francois |
| 2017/0308648 | A1* | 10/2017 | Clarke .................. G16H 10/60 |
| 2018/0018434 | A1* | 1/2018 | Assan ................. G06F 21/6218 |
| 2019/0108909 | A1* | 4/2019 | Lee .................... G01C 21/3679 |
| 2020/0013497 | A1* | 1/2020 | Aydelotte ............... G16H 80/00 |
| 2021/0020307 | A1* | 1/2021 | Bhimavarapu .... G06Q 10/1097 |
| 2021/0295985 | A1* | 9/2021 | Prokle .................... G06Q 10/06 |

OTHER PUBLICATIONS

"Smart Devices in Health Care", at least as early as Nov. 29, 2017, pp. 1-8.

MobileSmith, "12 Hospital Apps for Quick ROI, Mobile Use cases that Will Solve Real Problems—Fast!", MobileSmith, 2016, pp. 1-15.

Deitrick et al., "Dance of the Call Bells, Using Ethnography to Evaluate Patient Satisfaction With Quality Care", Journal of Nursing Care Quality, Aug. 23, 2006, pp. 316-324, vol. 21, No. 4, Lippincott Williams & Wilkins, Inc.

Kuruzovich et al., "Wireless Communication Role in Patient Response Time", CIN: Computers, Informatics, Nursing, 2008, pp. 159-166, vol. 26, No. 3, Wolters Kluwer Health, Lippincott Williams & Wilkins.

* cited by examiner

SOFTWARE APPLICATION FOR PATIENT CARE AND RELATED DEVICE, SYSTEM, AND METHOD

CLAIM OF PRIORITY

This application claims priority to U.S. Provisional Patent Application Ser. No. 62/745,242, which was filed Oct. 12, 2018, and which is titled "Application for Patient Care and Related Device, System, and Method," and which is incorporated by reference herein.

SUMMARY

In an embodiment, an electronic device includes a display screen, a memory circuit, and computing circuitry, which is coupled to the display screen and to the memory circuit, and which is configured to cause the display screen to display icons that are each related to respective data regarding a patient at a medical facility, to retrieve, from the memory, the respective data in response to a user of the electronic device selecting, via the display screen, a corresponding one of the displayed icons, and to cause the display screen to display the retrieved respective data.

Such a device (e.g., a smart phone), and medical-stay-related software application that the device is configured to execute, can facilitate the stay of a patient in a medical facility in a number of ways. For example, the device can be configured to provide the patient information about his/her stay, such as his/her schedule (e.g., diagnostic appointments, visits by members of his/her healthcare team), medications, and procedures. Furthermore, the device and software application can be configured to allow a patient to grant others (e.g., friends and family members) access to the patient information. For example, family members can install the software application on their devices, and the patient can grant the family members access to his/her schedule via his and their devices and software applications so that they know when the patient is in his/her room and can accept visitors; and such access can be granted securely, for example, by use of a confirmation code that the patient sends to the family members devices via his/her device, thus reducing the potential for an unauthorized user to gain access to the patient's information. Moreover, the patient can choose what information that each family member/friend is authorized to view; for example, the patient may grant a friend access only to the patient's schedule so that the friend can plan a visit. In addition, the device and software can be configured to allow a patient to submit questions regarding his/her care to a doctor or other member of the patient's healthcare team. An intranet version of the software application running on, e.g., a server or other computer system of the hospital, can allow hospital staff to enter and change the patient information as needed, and to broadcast the information and changes to the devices and software applications of the patient and of all other authorized users. A physician version of the application running on a device (e.g., smart phone) of a doctor can be configured to allow the doctor to answer the patient's questions and to send information to the patient and other uses of the application, for example, to send a time at which the doctor anticipates checking in on the patient. And all devices running all versions of the software application can be configured to encrypt the patient's data in the devices' memories and during transmitting the patient's data from one device to another device.

DETAILED DESCRIPTION

Figure 1:
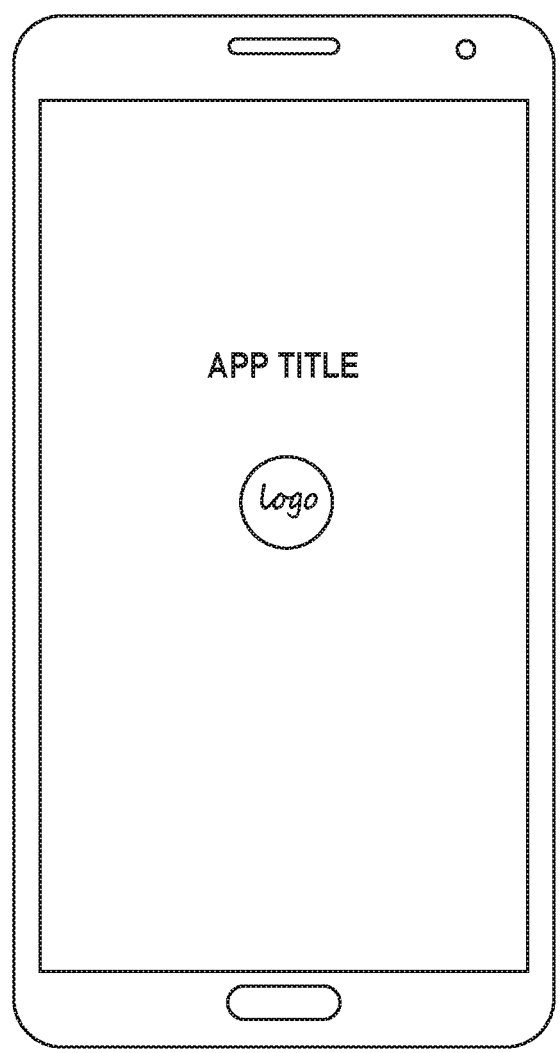
FIG. 1 is a screen view of an electronic device that is configured to execute instructions of a medical-stay-related software application, and to display, in response to the executed instructions, a title screen or page of the software application, according to an embodiment.

In the forgoing, a hospital is described as a medical facility at which a patient stays for medical treatment, it being understood that the forgoing applies to any suitable medical facility (e.g., outpatient facility) other than a hospital. Being a patient in an inpatient or outpatient hospital setting can be a very difficult experience. There are frequently many health-care providers (e.g., physicians, nurses, technicians) involved with the care of a patient, making it easy for a patient to feel confused and vulnerable. Poor communication with patients often will lead to poor satisfaction scores, such as Hospital Consumer Assessment of Healthcare Provider and Systems Score (HCAHPS score). Currently where medical-insurance (e.g., Medicare) reimbursement is closely tied to patient satisfaction, finding ways to optimize the patient experience behooves all health-care providers and institutions. According to a Pew research study from 2016, 77% of Americans have a smartphone.

Therefore, one can harness this technology to improve patients' experiences during a stay at a hospital or at another medical facility.

Described herein are one or more embodiments of a mobile software application (hereinafter "software application" or "App") that puts a patient and authorized family members at the center of the communication loop, and radically improves both the patient's and family members' medical-stay experience. In an embodiment, the App is configured to coordinate with a facility's (e.g., hospital's) Electronic Medical Record (EMR) system to draw some of the desired information for functionality, thereby reducing the amount of manpower typically used to keep such a mobile software application operational. In an embodiment, the App will be very user friendly to physicians and other healthcare providers so that using the App does not increase their workloads. Furthermore, although hereinafter the App is described as being configured to perform functions and operations, it is understood that a device, such as a smart phone, that is programmed with the App is configured to perform the functions and operations attributed to the App by executing program instructions that form the App. Moreover, although a smart phone is described such the device hereinafter, it is understood that the App may be installed on, and run on, any other suitable device such as a palm computer, tablet computer, laptop computer, smart watch, and desktop computer.

In an embodiment, prior to, when, or shortly after a patient arrives at the hospital, he/she, and his/her family members and friends, will receive information on how to download the Health Insurance Portability and Accountability Act (HIPPA) compliant App to improve his/her hospital experience. For example, the App, and information regarding how to download the App to a smartphone, may be advertised, e.g., via posters in a doctors' office, during the pre-check-in procedure or in the pre-check-in documents at the hospital, and via posters in the check-in/waiting area at the hospital. Alternatively, the patient, a family member, or a friend may have already received information on how to download the App, or may already have installed the App on his/her smartphone. For example, the patient may have received such information in a pre-check-in communication (e.g., email, text) from the hospital or from another healthcare provider such as the referring provider.

The App is configured to function as the communication hub for the patient, and the patient's family, nurses, physicians, social workers, physical therapists, and other members of the patient's health-care team. The patient can utilize the App during his/her inpatient hospitalization to help him/her achieve better communication with members of his/her healthcare team, family, and circle of friends, and a better understanding of what will be happening to him/her in the hospital. In addition to improving communication, which will translate into higher patient-satisfaction scores, the App is also something that the patient can use when he/she is not in the hospital, to help keep better track of his/her medical history and medications. In addition, family members can use the App during a patient's outpatient surgical procedure(s) to help the patient's family understand when surgery is started and when it is completed (for example, so that a family member can arrange for transportation to take the patient home from an outpatient clinic). The App can be configured to have different functionality depending on the category of the user of the App. For example, the App can be configured to present, to a patient, a menu that is different than a menu that the App is configured to present to a member of the patient's family, and that is different than a menu that the App is configured to present to a friend of the patient.

A good patient experience is one where the patient understands why he/she is in the hospital, who is helping to take care of him/her, and what each of the patient's care providers' roles are in the patient's care. After the patient downloads the App to his/her smart phone, the patient can send invitations to download and install the App to family members and friends via text or e-mail. After a family member or friend downloads and installs the App on his/her smart phone, the family member or friend can access some, or all, of the information that the patient will be receiving via the App installed on the family member's or friend's smart phone. For example, the patient can, via the App installed on the patient's smart phone, limit the information to which a family member or friend has access via the App installed on the family member's or friend's smartphone. Therefore, a family member or friend, particularly one who is not in the geographic area of the patient, can feel, via the App, integrated in the patient's inpatient hospital experience.

To download the App to, and to install the App on, his/her smart device, a patient receives a text message, e.g., from the medical facility in which he/she is being treated, with a link to a location (e.g., an online store) from which he/she can download the App. The text message may include a personal identification number (PIN), which the patient may need to download and install the App. The patient may then forward the text to family and friends so that they too can download and install the App onto their respective smart devices. Alternatively, as described below, the App may include a feature that allows a patient to invite family and friends to download and to install the App.

Referring to FIG. 1, in an embodiment, after the App is installed on one's smart device, in response to one opening the App on his/her smart device (e.g., smart phone, tablet, laptop, computer), the App causes the device to display a title page for a predetermined amount of time, such as three seconds.

Figure 2:
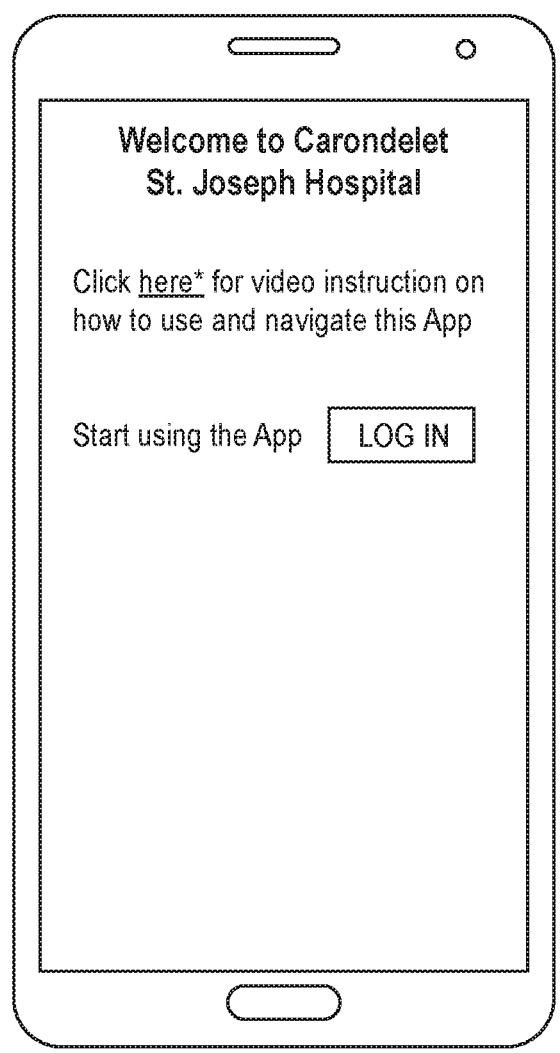
FIG. 2 is a screen view of an electronic device that is configured to execute one or more instructions of a medical-stay-related software application, and to display, in response to the executed one or more instructions, a welcome and login page including a link to written instructions for using the software application, according to an embodiment.

Referring to FIG. 2, in an embodiment, after ceasing generation of the title page, the App causes the device to display a welcome-and-login page, which may also include a link to instructions (e.g., a video) on how to use the App and on how to register and set up one's login credentials.

Figure 3:
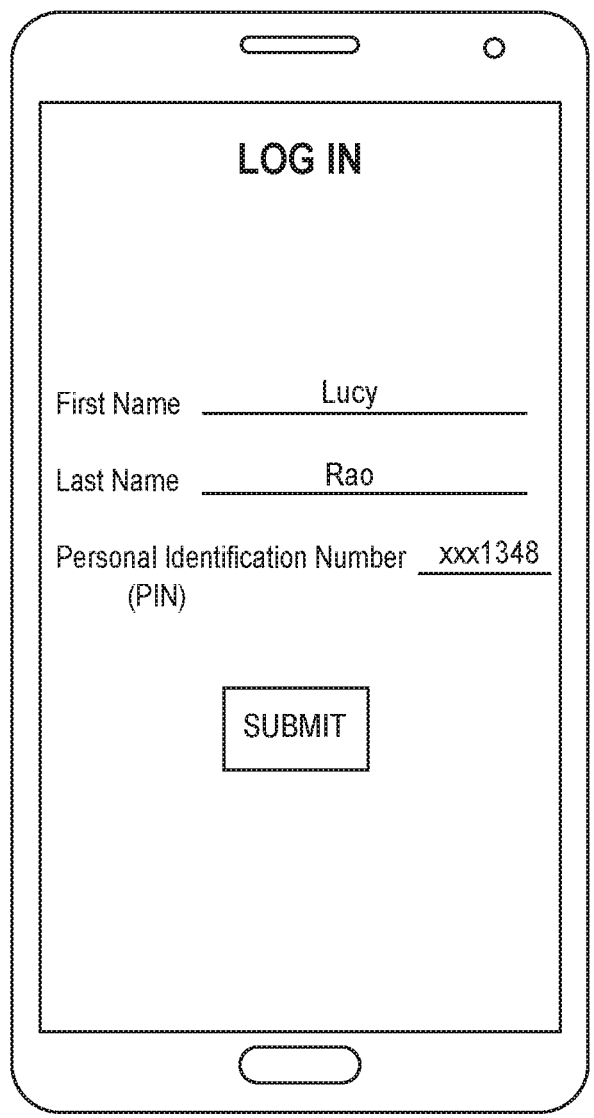
FIG. 3 is a screen view of an electronic device that is configured to execute one or more instructions of a medical-stay-related software application, and to display, in response to the executed one or more instructions, a log-in page, according to an embodiment.

Referring to FIG. 3, in an embodiment, in response to one selecting a "log in" button on the welcome-and-login page of FIG. 2, the App causes the smart device to display a log-in screen. The App user enters his/her credentials, such as name and PIN or a password, and then selects a "submit" button. If the App recognizes the credentials, then the App causes the device to display a home page that includes one or more icons as described below in conjunction with FIG. 38 (FIG. 38 is a better home screen figure).

Figure 38:
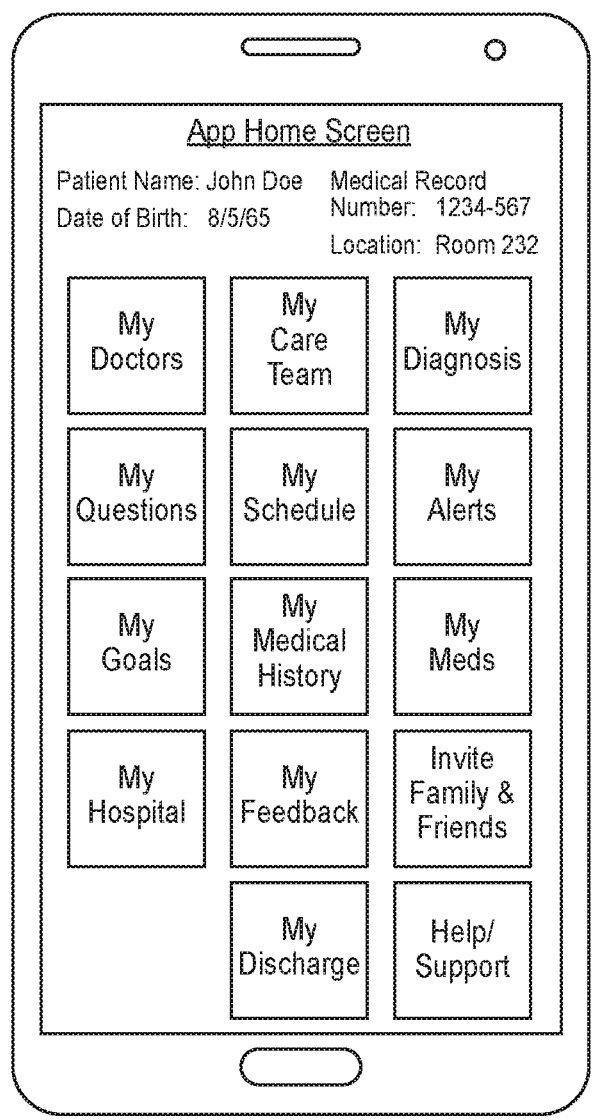
FIG. 38 is a screen view of an electronic device that is configured to execute one or more instructions of a medical-stay-related software application, and to display, in response to the executed one or more instructions, a home screen of the software application, according to an embodiment.

FIG. 38 is the electronic device displaying a home page, or home screen, of the App, according to an embodiment.

Figure 5:
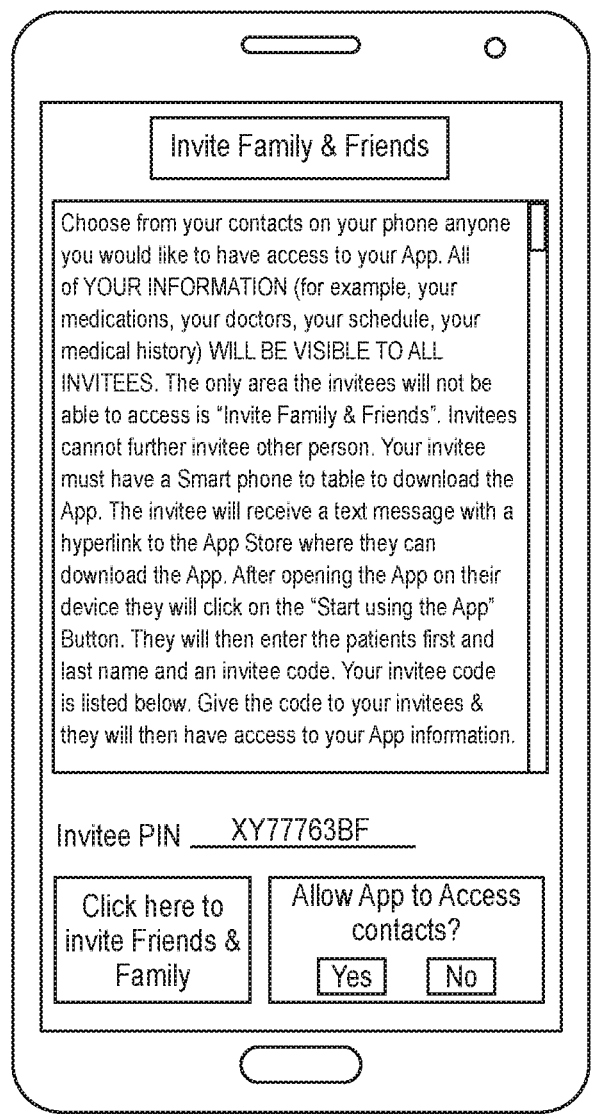
FIG. 5 is a screen view of an electronic device that is configured to execute one or more instructions of a medical-stay-related software application, and to display, in response to the executed one or more instructions, a page that allows a patient to invite other people, including the patient's family and friends, to download and install the software application, according to an embodiment.
Figure 6:
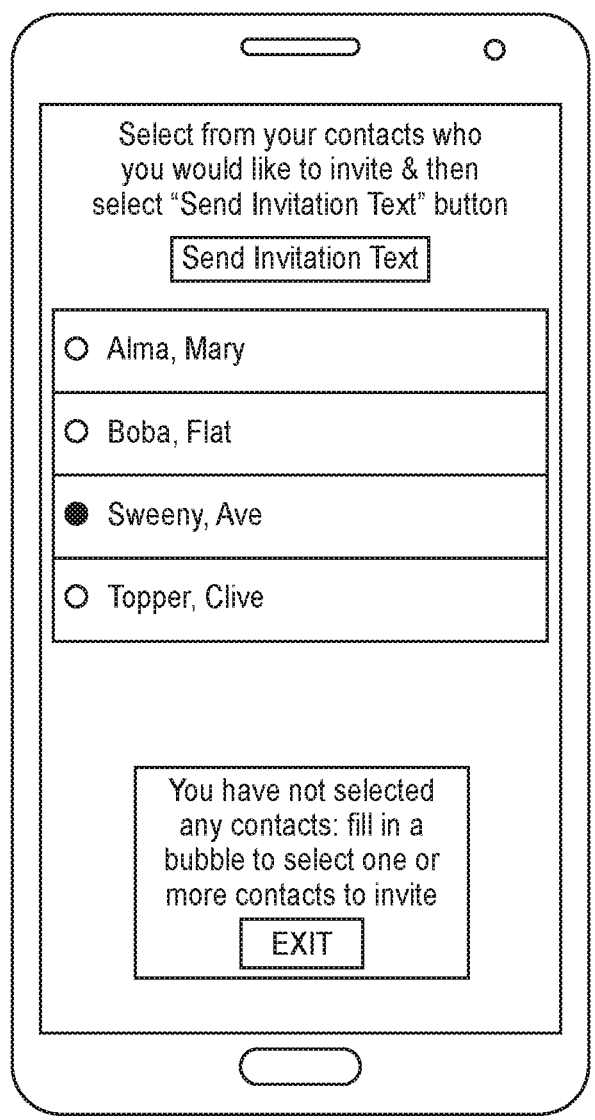
FIG. 6 is a screen view of an electronic device that is configured to execute one or more instructions of a medical-stay-related software application, and to display, in response to the executed one or more instructions, a page that allows a patient to invite other people to download and install the software application from a contact list of the patient, according to an embodiment.

Referring to FIGS. 38, 5 and 6, in an embodiment the App causes the device to display a page with a button that allows a patient to invite family and friends to download and to install the App on their own smart devices, and, referring to FIG. 6, the App may allow the patient to invite family and friends from a contacts list stored on the patient's smart device or another device to which the smart device has access. The App may also allow the patient to invite persons who are not family or friends, or who are not listed in one of the patient's contact lists. Furthermore, the App may cause the device to display a warning that invitees who download and install the App on their smart devices will have access to medical, and other personal, information of the patient that the App makes available.

Figure 7:
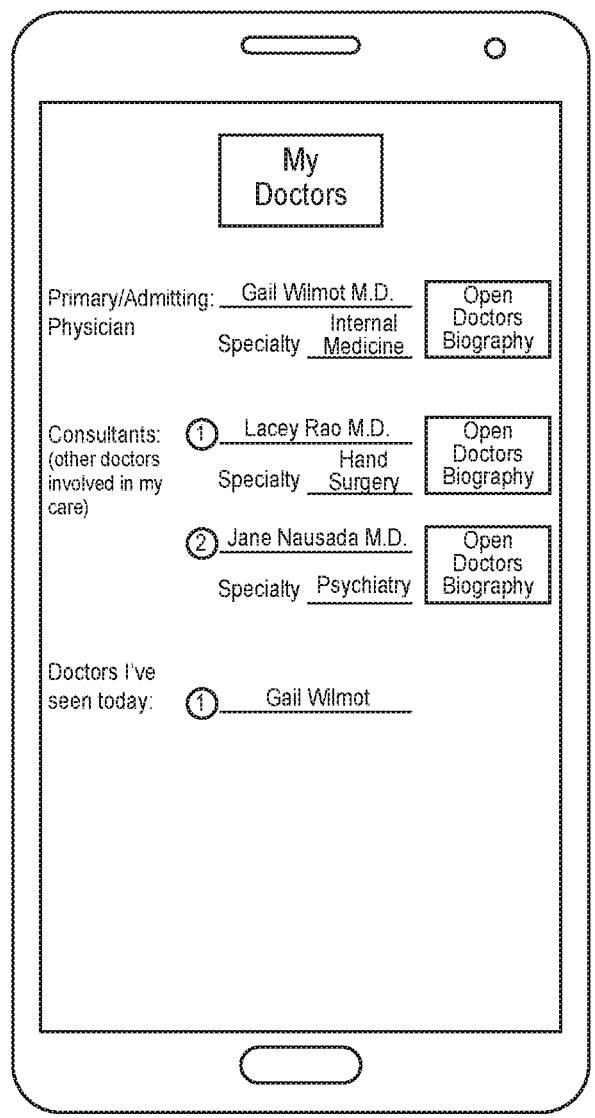
FIG. 7 is a screen view of an electronic device that is configured to execute one or more instructions of a medical-stay-related software application, and to display, in response to the executed one or more instructions, a "My Doctors" page that lists some or all of the physicians caring for the patient during the medical stay, according to an embodiment.
Figure 8:
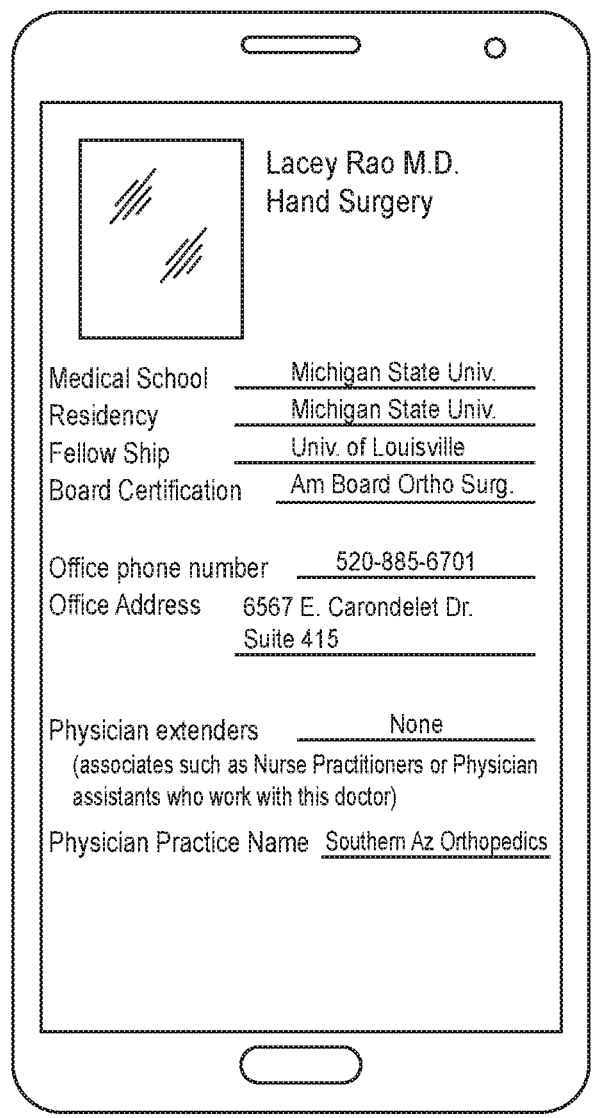
FIG. 8 is a screen view of an electronic device that is configured to execute one or more instructions of a medical-stay-related software application, and to display, in response to the executed one or more instructions, a page that includes information regarding a respective one of the patient's medical practitioners, according to an embodiment.

Referring to FIGS. 38 and 7, in an embodiment, one of the prime functions of the App is to allow a patient to be able to better understand exactly who makes up his/her medical-treatment team. The home page (FIG. 38) of the App causes the smart device to display a "My Doctors" tab that, when selected (e.g., by "pushing" the tab on a device's touch screen), lists all physicians and other healthcare professionals caring for the patient. Referring to FIG. 7, under the "My Doctors" tab a "Primary Doctor" listed, and any specialists or other consultants that are called to see a patient can be added by the hospital clerks or the staff of the emergency room (ER) if the patient was admitted via the ER. Referring to FIG. 8, also via the "My Doctors" tab, the patient may have access, for example, to a photo of each physician, involved with his/her care, each physician's biographical information, and a brief explanation of that physician's role in the patient's care. A physician's biographical information can also include a list of Nurse Practitioners, Physician's Assistants, or Resident Physicians who are associated with the physician and who may be rounding with/for the physician. This information, such as the photos and bios of the patient's physicians and other providers, can be accessible via a displayed link to a server (e.g., a cloud server) on which this information is stored, or the App can cause the smart device on which the App is installed to download and to store this information on local memory onboard the smart device. And the smart device's display of this information can include further links, such as to a treating physician's website.

Still referring to FIGS. 38 and 7-8, there are certain members of the healthcare team, such as nurses and Hospitalists, who rotate on a daily basis, and such rotations can make it confusing and difficult for the patient to keep track of his/her healthcare providers. To reduce or to avoid such patient confusion and difficulty, each day, instead of using a dry erase board in the patient's hospital room to list the patient's nurse, Patient Care Assistant (PCA), Hospitalist, etc., a member of the patient's healthcare team, or other hospital staff, can enter this information through the App installed on the physician's smart device, or through a separate computer based intranet version of software application for all non-physician providers. So, this information (e.g., which providers visited the patient on a particular day) is provided to the patient's App, and family and friends' Apps. Frequently, a patient has several different physicians involved in his/her care, and this can also be confusing for the patient and his/her family and friends to understand why a certain type of physician is part of the patient's healthcare team. Also, a patient frequently does not know to whom to address his/her questions. Therefore, the App can provide the above-described information so that the patient, family, and friends can understand and delineate the roles that each provider plays in the patient's care, and to help the patient to understand which physician would best address a particular set of one or more questions.

Figure 4:
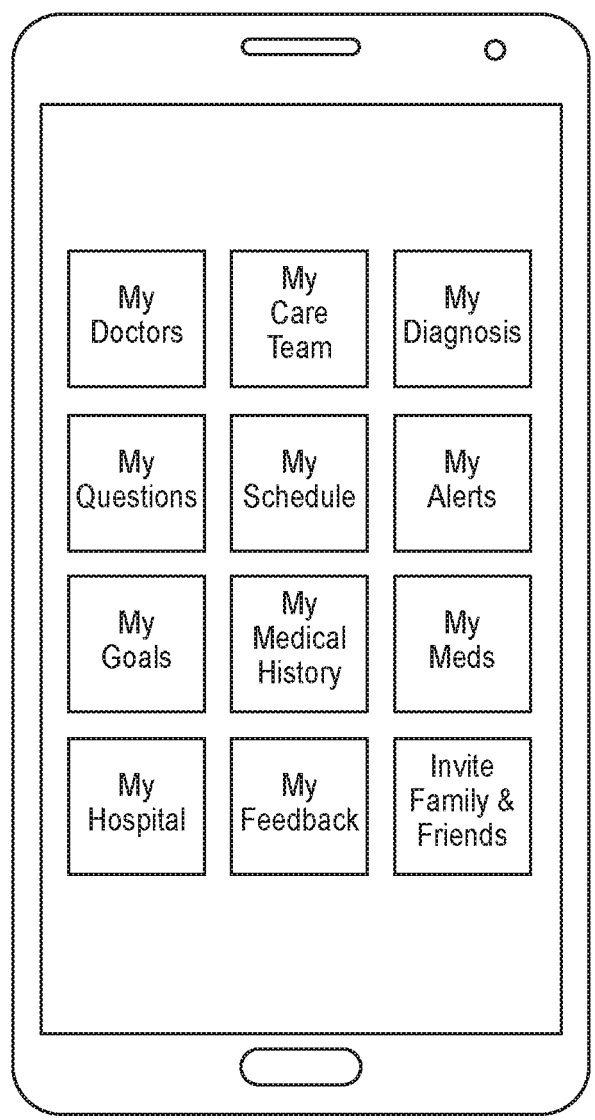
FIG. 4 is a screen view of an electronic device that is configured to execute one or more instructions of a medical-stay-related software application, and to display, in response to the executed one or more instructions, a home page, according to an embodiment.
Figure 9:
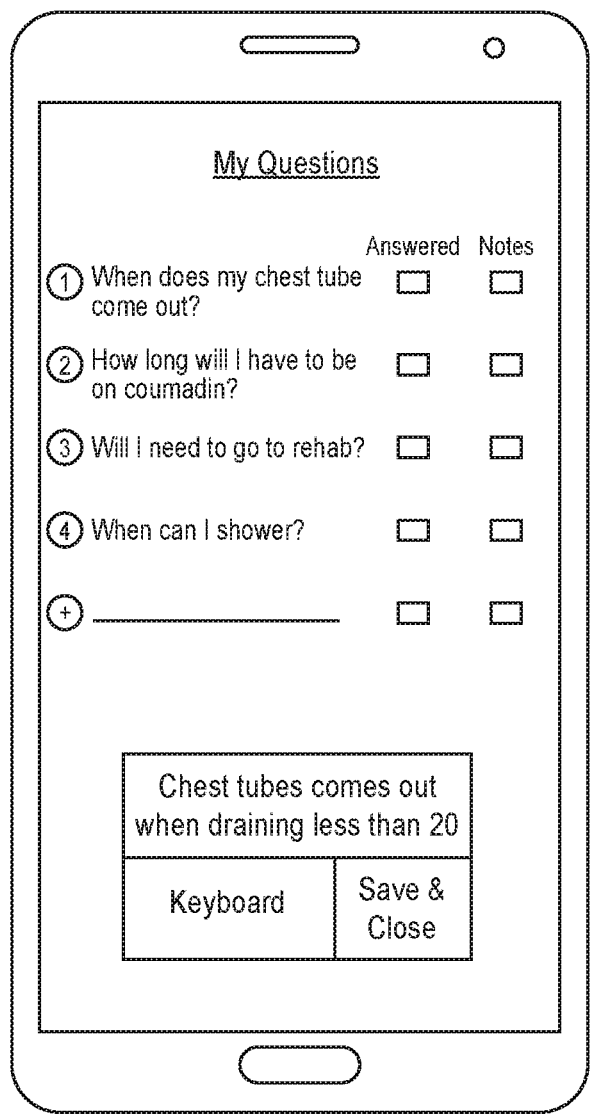
FIG. 9 is a screen view of an electronic device that is configured to execute one or more instructions of a medical-stay-related software application, and to display, in response to the executed one or more instructions, a page via which the patient can submit questions to his/her medical-care team, according to an embodiment.

Referring to FIGS. 4 and 9, the App includes a "My Questions" tab via which the patient, his/her family members, or friends, can submit a list of one or more questions as they arise. These questions are visible to some or all members of the healthcare team using the App (or a compatible provider application) who would like to review and answer the questions. Often the patient, family, or friends, have questions, and the App is configured to allow the patient, family members, and friends to memorialize their questions in writing at the time the questions arise. Those whom the patient has invited to download and install the App, and to use the App to keep track of the patient's progress, such as a patient's son or daughter located in a different state from the patient, can be granted (by the patient, or durable power of attorney) access to the "My Questions" tab, and, therefore, can view the patient's questions and can enter any questions of their own or of other family members and friends. Furthermore, the App is configured to allow the patient, family members, and friends to save answers to their questions either in memory local to their respective smart devices or on a server (e.g., a cloud server) maintained, for example, by the App provider or by the medical facility in which the patient is staying.

Referring to FIGS. 4 and 10-13, the home page of the App includes "My Alerts" and "My Schedule" icons, according to an embodiment. The App is configured to improve communication regarding when a patient will be, or is likely to be, seen by members of the healthcare team, and when appointments for procedures like physical therapy and imaging studies are scheduled during the day. Frequently, a family member is not present at the time of a practitioner visit, but he/she has questions for the practitioner such as a physician, social worker, or physical therapist. A common scenario is a patient's family member was "just there" but left right before the physician comes to see the patient. By alerting the patient and the family member that the physician will be coming to see the patient shortly, the family member has the opportunity to stay until the physician arrives, and to be involved in any discussions regarding the physician's plan of care for the patient. The App could send an alert to the patient and family member, the alert indicating which physician is coming and approximately in what time window he/she will be arriving.

Referring again to FIG. 4, in the medical-professional, family-and-friend, and intranet configurations of the App, the icons may include the word "Patient's" instead of "My." For example, instead of "My Doctors," the icon may include the words "Patient's Doctors" in all but the patient configuration of the App. Alternatively, the word "My" may appear in the icons of all configurations of the App, it being understood that "My" refers to the patient.

Figure 14:
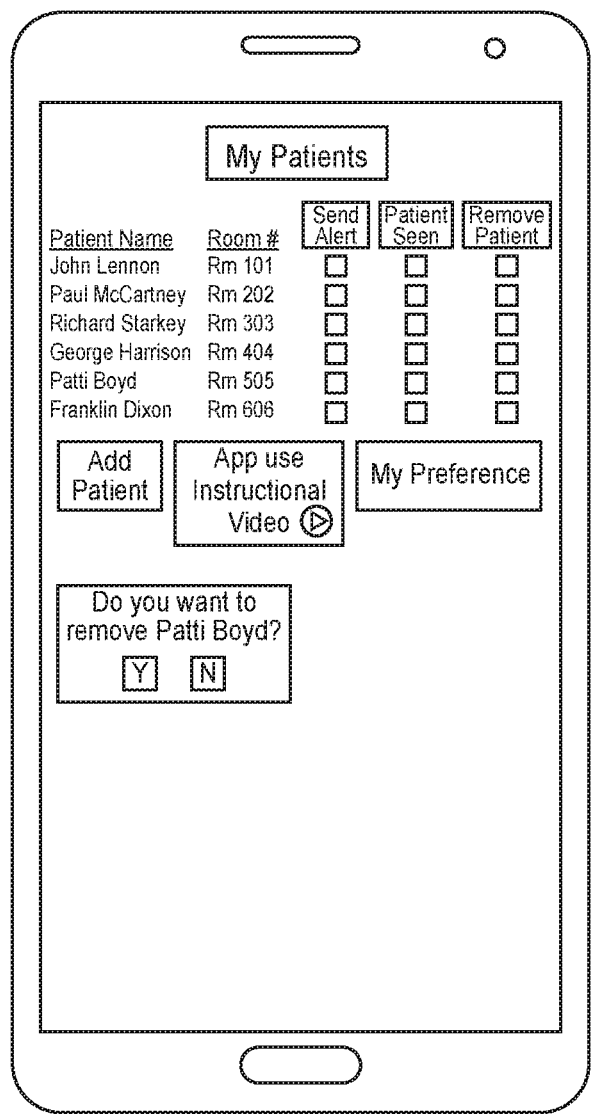
FIG. 14 is a screen view of an electronic device that is configured to execute one or more instructions of a medical-stay-related software application, and to display, in response to the executed one or more instructions, a "My Patients" page that includes a list of patients assigned to a corresponding member of a patient's healthcare team at a medical facility, according to an embodiment.
Figure 15:
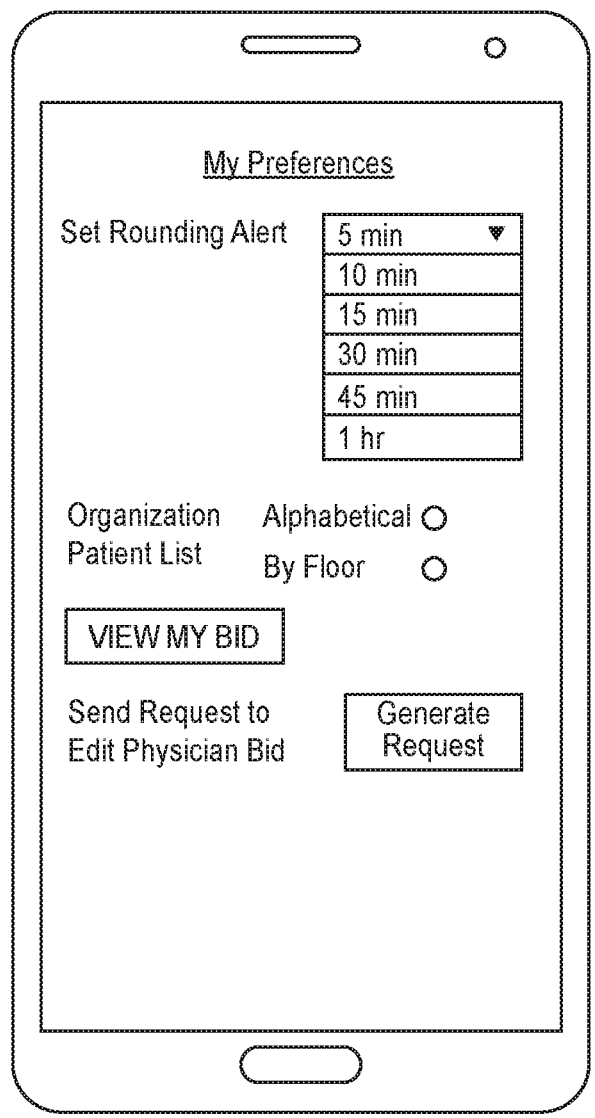
FIG. 15 is a screen view of an electronic device that is configured to execute one or more instructions of a medical-stay-related software application, and to display, in response to the executed one or more instructions, a page that allows a physician or other health care provider to determine how alerts from the medical professional to the patient are handled, according to an embodiment.

Referring to FIGS. 14-15, the physician can send, easily and quickly, an alert to one, or multiple patients, using the App from the physician's smartphone, the physician's App being configured for a physician or other practitioner or medical professional instead of for a patient. A physician's schedule can be inconsistent and subject to change, and, therefore, the physician is not always able to round at the same time every day, so a patient is often left having no idea when his/her doctor(s) will see him/her. For a surgeon, there is sometimes a gap between his/her surgeries during which he/she has an opportunity to see a patient. The physician can configure his/her App to give the physician the flexibility to alert the patient and his/her family and friends when the physician is planning to see the patient. For example, a physician can pull up a list of his/her patients on his/her smart phone using the App, and send alerts to the various patients that he/she plans on seeing within the next period of time, e.g., the next 30 min. This allows family members and friends a better opportunity to be present during the physician's visit with the patient.

Still referring to FIGS. 14-15, it is often impractical to let a patient know the exact time of each physician's visit, imaging study, Physical Therapy (PT) session, etc., but the App provides an improvement to the conventional notification procedure. For example, if a patient is scheduled for an imaging procedure, a push notification comes to the patient's App with a written message, for example, "Your imaging study is scheduled to tentatively occur at 5:30 pm." Or, if the surgery department schedules an inpatient procedure, the surgery department could send an alert to the patient's App that states, "Your surgery has been scheduled for 8:30 a.m. on Jul. 3, 2017." For example, a clerk would enter this information, and initiate the push, using the App installed, for example, on the clerk's desk computer or other device. Or, the App provider may provide an internet-accessible dashboard in which the clerk can enter the procedure-scheduling information and initiate the push of the notification to the patient's and family member's Apps.

Figure 16:
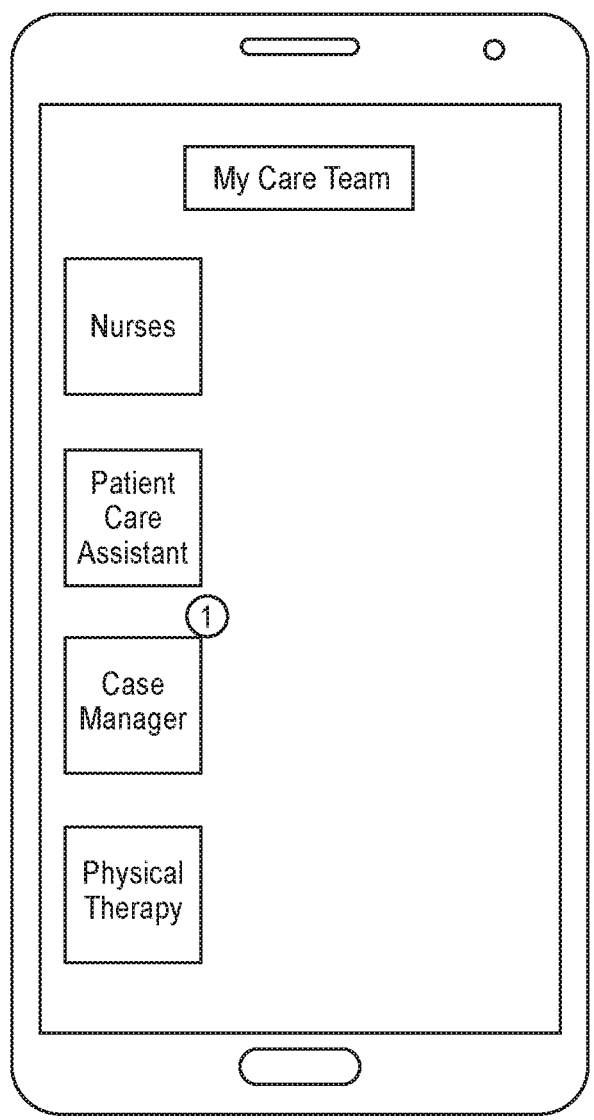
FIG. 16 is a screen view of an electronic device that is configured to execute one or more instructions of a medical-stay-related software application, and to display, in response to the executed one or more instructions, lists categories of healthcare team members assigned to the patient, according to an embodiment.
Figure 17:
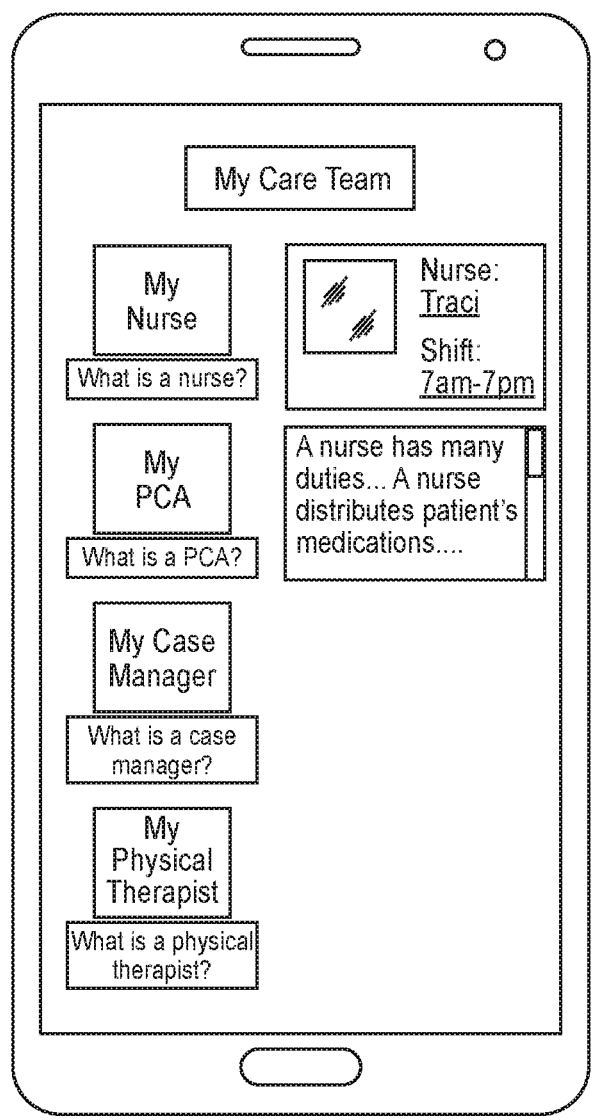
FIG. 17 is a screen view of an electronic device that is configured to execute one or more instructions of a medical-stay-related software application, and to display, in response to the executed one or more instructions, that includes icons that allow a patient to request and view additional information about the healthcare team members assigned to the patient, according to an embodiment.
Figure 18:
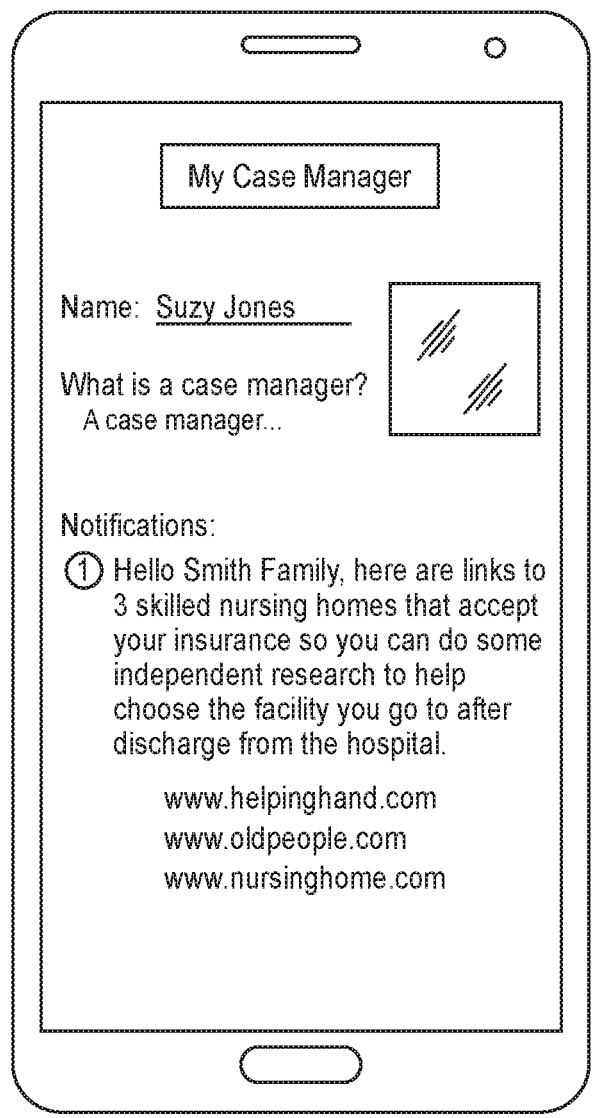
FIG. 18 is a screen view of an electronic device that is configured to execute one or more instructions of a medical-stay-related software application, and to display, in response to the executed one or more instructions, additional follow-up information regarding the information displayed per FIG. 17, including website hyperlinks, to the patient, according to an embodiment.

Referring to FIGS. 16-18, a patient may work with a case manager and/or social worker in the hospital setting. This is another area in which the App is configured to improve communication. The patient's App can include tabs or links (e.g., www.helpinghand.com) to connect the patient to information available on a health-provider website or on the internet in general. For example, a patient can be discharged from a hospital to a Skilled Nursing Facility (SNF) or Rehab Facility—links to those facilities' websites can be placed in a section of the patient's, family members', and friends' Apps to help facilitate a patient's research into such institutions.

Furthermore, a social worker/case manager could also send, via his/her App to the patient's, family members', and friends' Apps, a notification of the approximate time that he/she anticipates rounding on a patient, so once again, family and friends can know when to be present if they desire to speak to the social worker/case manager.

Figure 13:
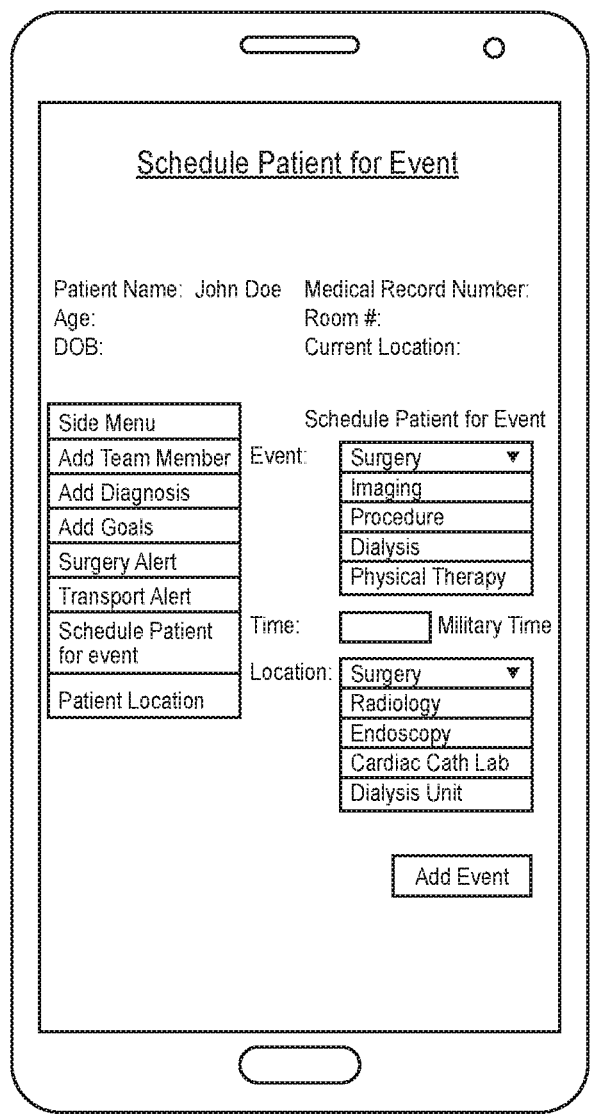
FIG. 13 is a screen view of an electronic device that is configured to execute one or more instructions of a medical-stay-related software application, and to display, in response to the executed one or more instructions, a page that allows a medical professional to schedule an event for a patient, according to an embodiment.
Figure 19:
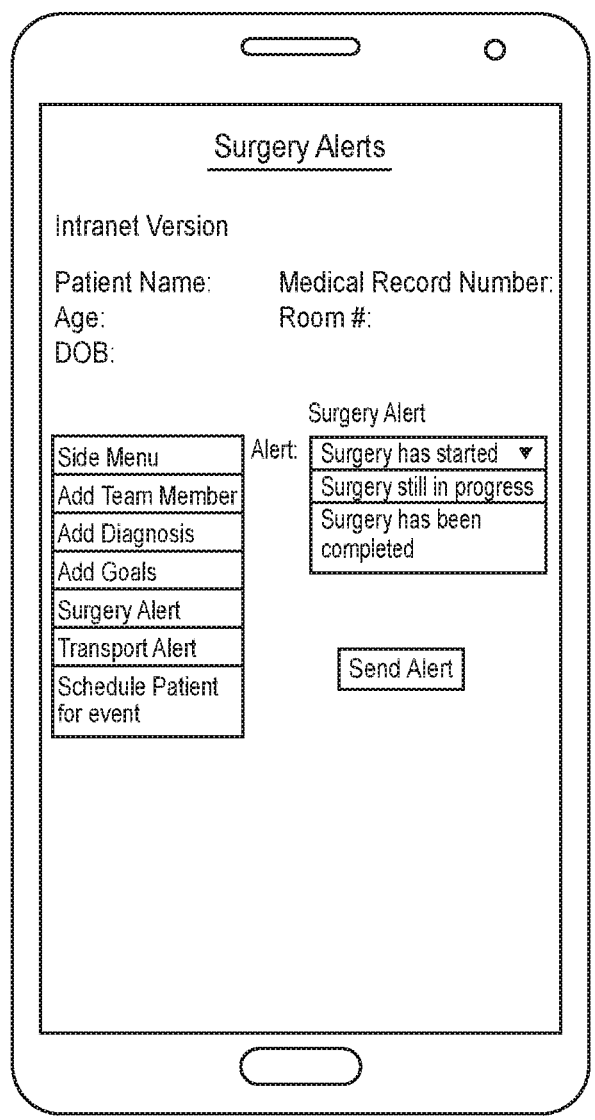
FIG. 19 is a screen view of an electronic device that is configured to execute one or more instructions of a medical-stay-related software application, and to display, in response to the executed one or more instructions, an alert menu that allows a medical provider to send alerts of a patient's progress to people the patient has invited to download the software application, according to an embodiment.
Figure 20:
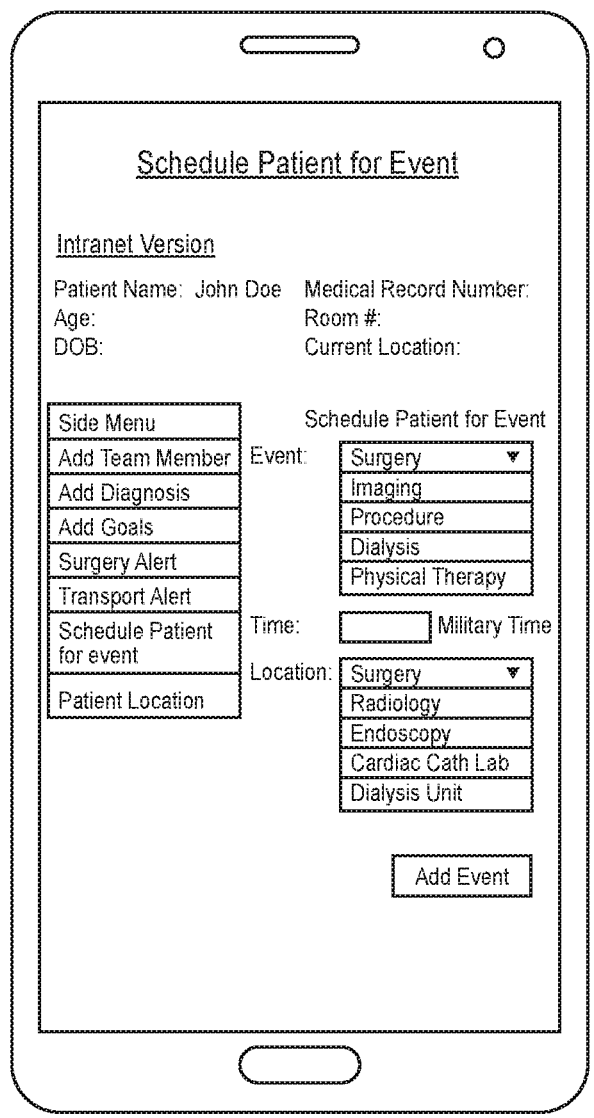
FIG. 20 is a screen view of an electronic device that is configured to execute one or more instructions of a medical-stay-related software application, and to display, in response to the executed one or more instructions, a menu that allows a physician or other healthcare team member to schedule an event for a patient, according to an embodiment.

Referring to FIGS. 13 and 19-20, in an embodiment, a department, such as Radiology Services, can notify a patient, via the patient's App, the general time that his/her imaging study, is scheduled to take place. The patient's App can be configured to give the patient a brief overview of what the procedure involves, thus demystifying the experience for, and alleviating potential fears of, the patient. The department can also push this notification to the Apps of family, of friends, and of one or more of the patient's medical-treatment providers. Such notification allows family members and friends to better plan their visits to the patient in the hospital so that they are able to spend time with the patient instead of merely sitting in the patient's room while the patient is undergoing a procedure or test such as an imaging study. And notification of when a patient is off the floor is also helpful to a physician as he/she plans his/her rounding. There is also a push notification of when the patient returns to the room. This notification allows family, friends, and healthcare providers to know when the patient is back in the room.

Still referring to FIGS. 13 and 19-20, in an embodiment, the App also can be configured to improve communications in the area of surgery, for example, to improve communications between the surgeon/hospital and the patient/family/friends.

In an embodiment, the Apps of family members and friends can be configured to track the progression of surgery on the patient to keep the patient's family and friends continually updated during the surgery. The Apps of family members and friends can be configured to alert family members and friends when surgery has started, when surgery has been completed, and when the patient reaches the after-surgery Post Anesthesia Care Unit (PACU). Family members and friends are often unaware of the preparation that occurs before the start of surgery due to things like positioning, anesthesia induction, and prepping of the patient. The amount of time that occurs before the actual start time/incision time can be significant, and family members and friends frequently become concerned because they were told a procedure may take a certain amount of time, and once that time has passed they may begin to worry. The circulating nurse can notify, via the App, the patient's family and friends when the surgery has actually started. Hospital staff can provide, via the App, updates to the family members and friends throughout the procedure. After surgery, the circulating nurse can send an alert to the Apps of the family members and friends that the patient is done with surgery and is heading to PACU. Such a notification allows family members and friends who might not be in the surgical waiting room to return, for example, from the cafeteria or another part of the hospital at an appropriate time to speak to the surgeon post operatively.

It can be important for a patient to ambulate after surgery.

Figure 21:
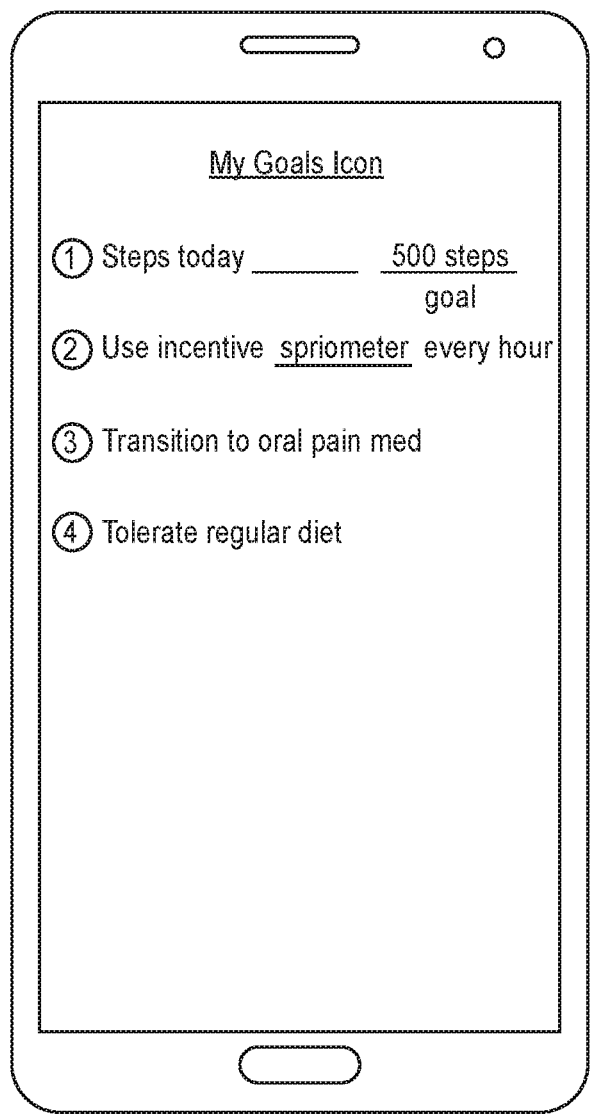
FIG. 21 is a screen view of an electronic device that is configured to execute one or more instructions of a medical-stay-related software application, and to display, in response to the executed one or more instructions, a list of treatment goals for a patient while staying in a medical facility, according to an embodiment.
Figure 22:
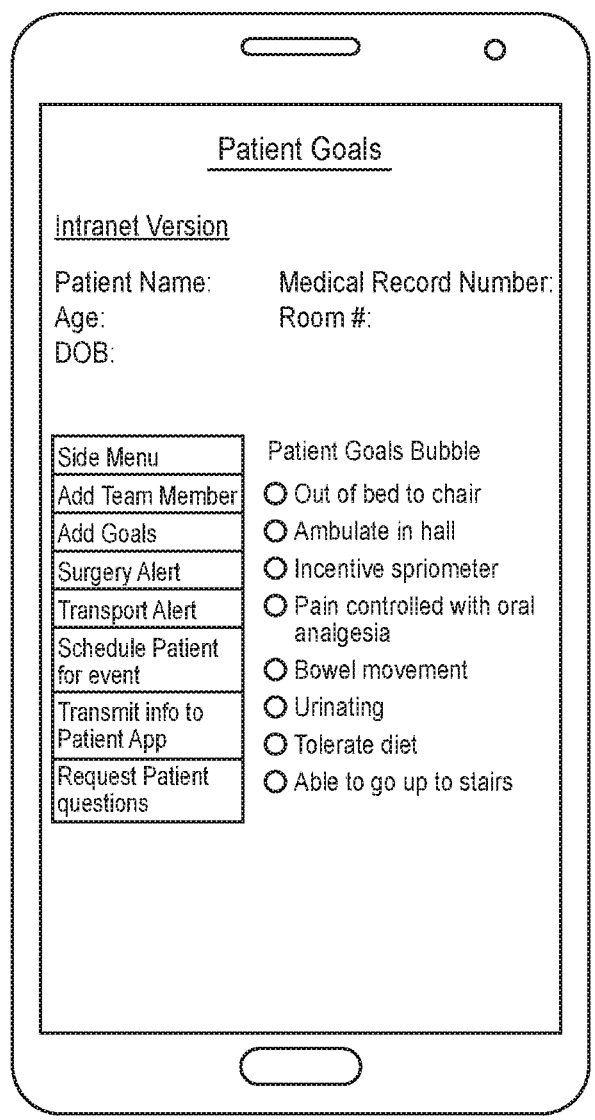
FIG. 22 is a screen view of an electronic device that is configured to execute one or more instructions of a medical-stay-related software application, and to display, in response to the executed one or more instructions, a menu that allows a physician or other healthcare team member for the patient to set goals, and to send the goals to the patient, according to an embodiment.

Referring to FIGS. 21-22, in an embodiment, the patient's App is configured to cause the patient's smart device to generate a pedometer feature to keep track of how many steps the patient has taken and what his/her steps-taken goal for the day is. The patient's App also pushes this information to the Apps of the physicians, nurses, physical therapists, and other members of the healthcare team so that they can monitor the patient's post-surgical progress.

Goals of Care are also something that the patient's App can be configured to help a patient achieve.

For example, a patient can be easily confused by what he/she should plan to accomplish during a given day in terms of diet, exercise, and rehabilitation.

Therefore, in an embodiment, the patient's App is configured to provide Daily Care Goals, which can be entered by a nurse or other patient-healthcare-team member, for example, from streamlined pick lists to help the patient understand what he/she should try and achieve on a particular day. Examples of goals from which a nurse can pick include 1) utilize incentive spirometer hourly, and 2) walk 500 steps today.

Figure 32:
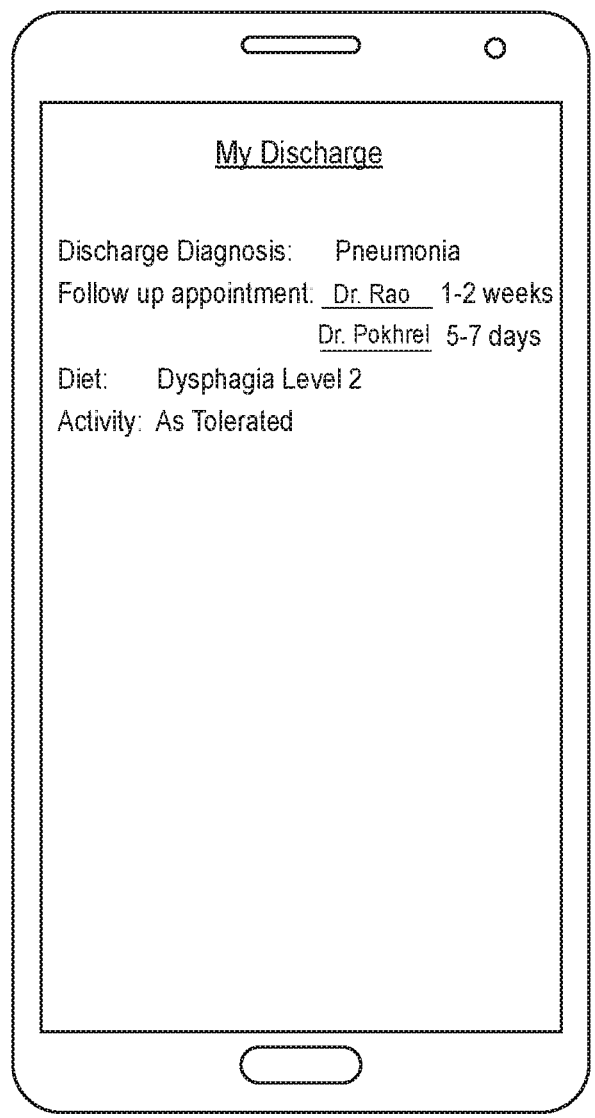
FIG. 32 is a screen view of an electronic device that is configured to execute one or more instructions of a medical-stay-related software application, and to display, in response to the executed one or more instructions, discharge instructions for a patient, according to an embodiment.

Referring to FIG. 32, in an embodiment, upon the patient's discharge from a hospital or other medical facility, the patient's App is configured to cause the patient's smart device to display discharge instructions (for example, "under" a "Patient Discharge" tab (not shown in FIGS. 23-24)) from the hospital or other medical facility that the patient can review. These instructions can be transferred to the patient's smart device from the EMR directly. The patient's App is configured to display a list of the one or more physicians that the patient should follow up with, as well as the time frame in which the patient should do so, and each physician's phone number. "Clicking" on a follow-up physician's name causes the patient's App to take the patient to a page that includes the physician's bio and office information. In the bio section, the patient's App is configured to include a link to the physician's web site. The patient's App also is configured to send a push notification, for example, one day after discharge, to remind the patient to schedule the requested follow-up appointment(s). For a patient that does not have certain providers, such as a Primary Care Physician (PCP), the patient's App can direct the patient to the discharging hospital's PCP network to help direct the patient to a quality PCP. Furthermore, the patient's App can cause the patient's smart device to display a list of one or more medications that the patient is to take after he/she is discharged, for example, under a "Discharge Medications" display tab or button.

In an embodiment, the patient's App is configured to function even after the patient is discharged from the hospital, to remind him/her about important health-related items such as yearly mammograms (for women patients), colonoscopies, medication schedules, etc. For example, for a female patient over the age of 40, the App can receive or generate, and cause the patient's smart device to display, a push notification that states, for example, "October is breast cancer awareness month. A yearly Mammogram is a very important part of your health care. We would be proud to serve you and to facilitate scheduling your yearly mammogram at (name) Hospital. Please call (xxx)xxx-xxxx and we can help schedule you for a screening mammogram. Thank you, and Be Well!"

Figure 23:
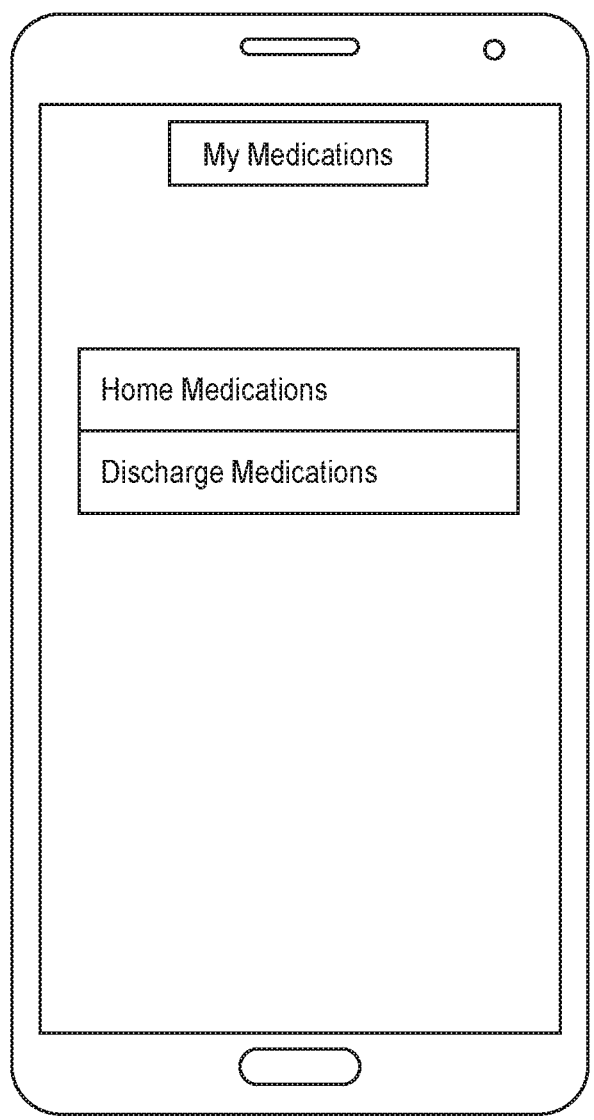
FIG. 23 is a screen view of an electronic device that is configured to execute one or more instructions of a medical-stay-related software application, and to display, in response to the executed one or more instructions, icons for lists of medications for a patient they were taking prior to admission to the health care facility "Home Medications" and a list of medications to be taken at home upon leaving the health care facility "Discharge Medications", according to an embodiment.
Figure 24:
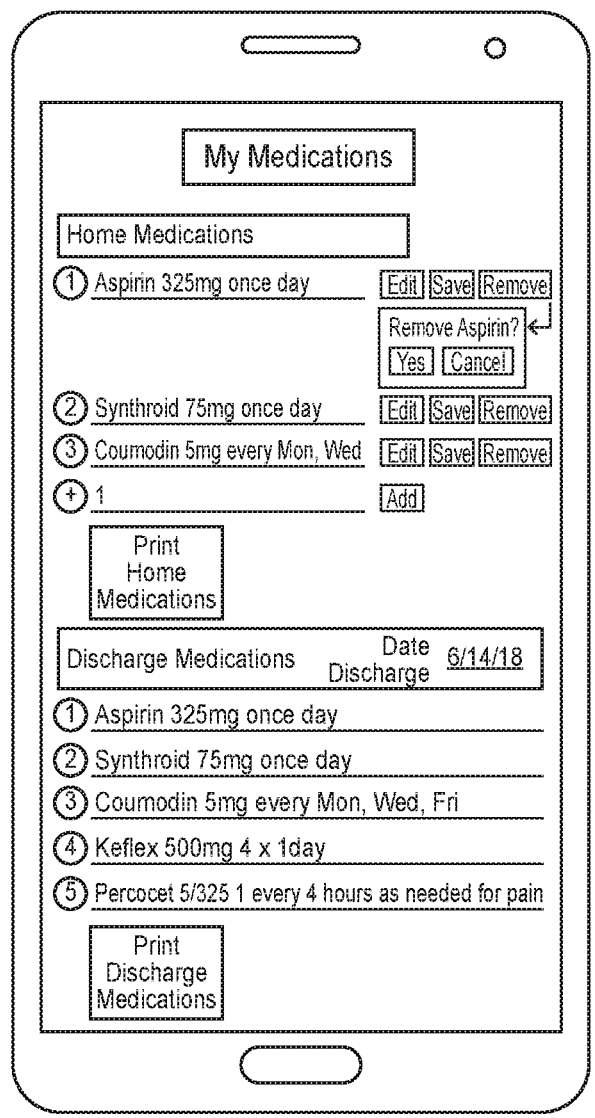
FIG. 24 is a screen view of an electronic device that is configured to execute one or more instructions of a medical-stay-related software application, and to display, in response to the executed one or more instructions, a list of medications for a patient to take after discharge from a medical facility, according to an embodiment.
Figure 25:
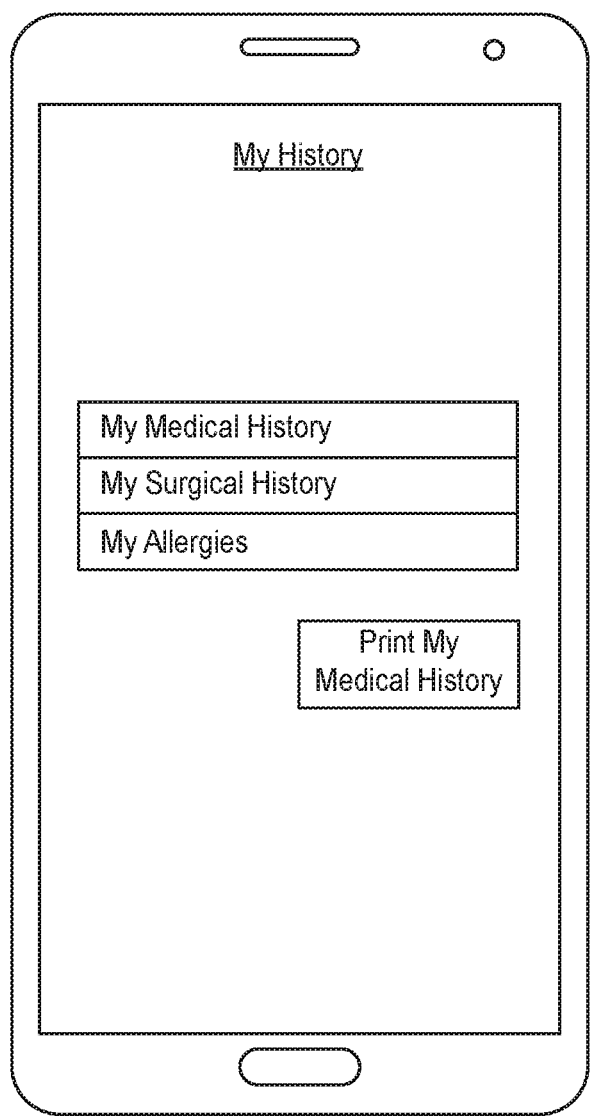
FIG. 25 is a screen view of an electronic device that is configured to execute one or more instructions of a medical-stay-related software application, and to display, in response to the executed one or more instructions, information regarding a patient's medical history, according to an embodiment.
Figure 26:
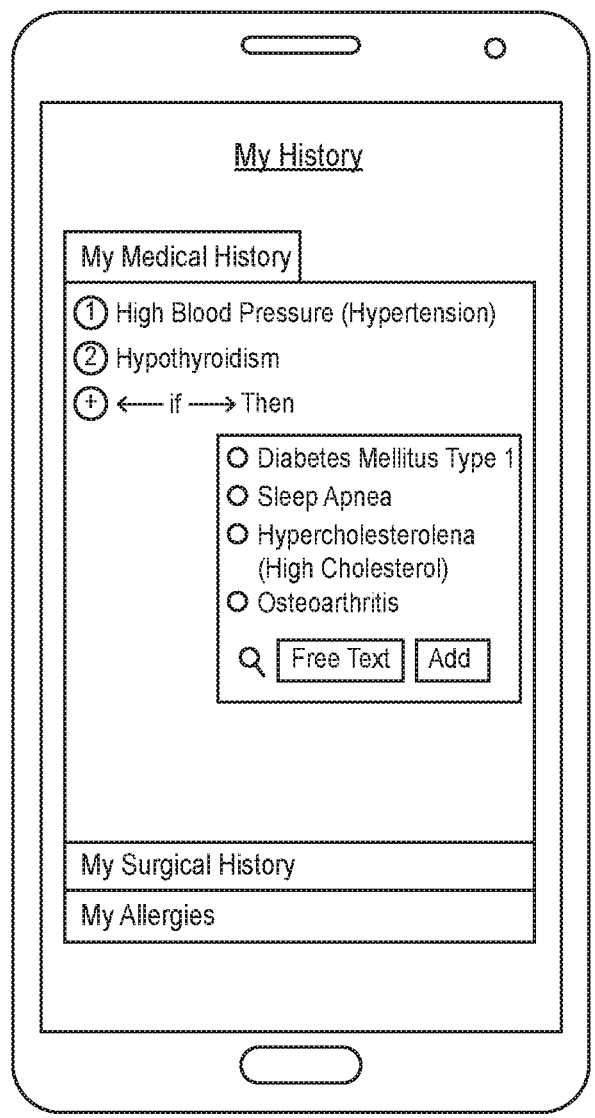
FIG. 26 is a screen view of an electronic device that is configured to execute one or more instructions of a medical-stay-related software application, and to display, in response to the executed one or more instructions, a detailed list of a patient's medical history, according to an embodiment.
Figure 27:
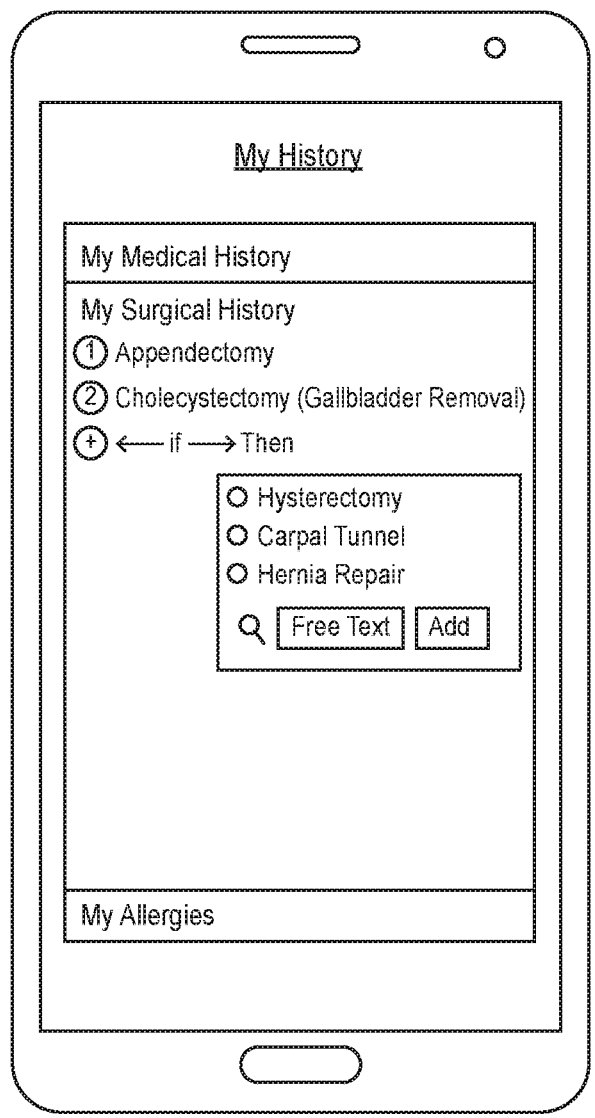
FIG. 27 is a screen view of an electronic device that is configured to execute one or more instructions of a medical-stay-related software application, and to display, in response to the executed one or more instructions, a patient's surgical history, according to an embodiment.
Figure 28:
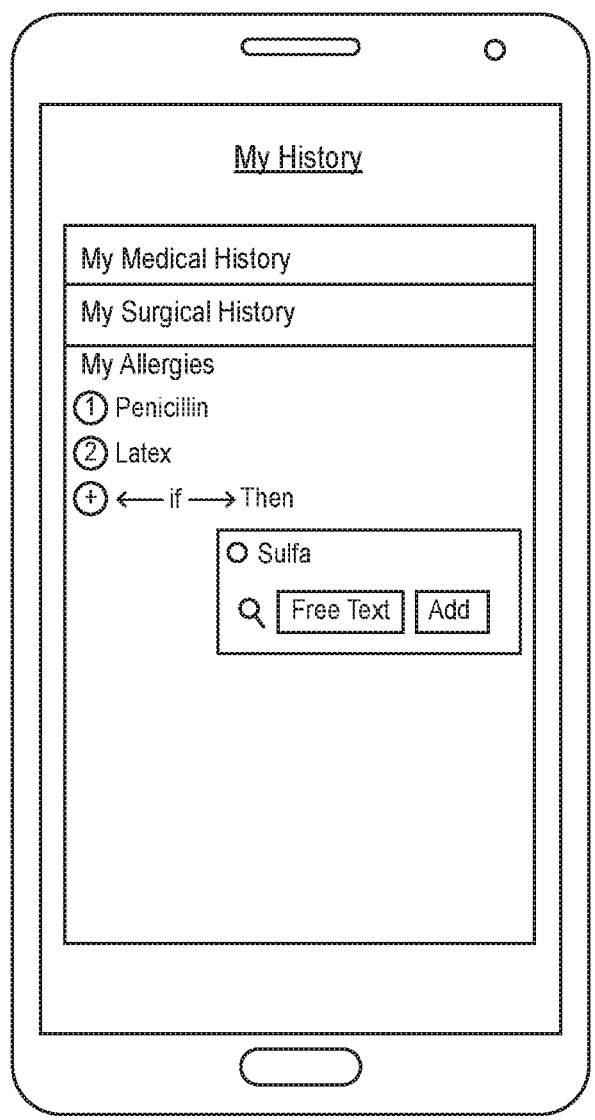
FIG. 28 is a screen view of an electronic device that is configured to execute one or more instructions of a medical-stay-related software application, and to display, in response to the executed one or more instructions, a list of a patient's allergies, according to an embodiment.

Referring to FIGS. 4 and 25-28, in an embodiment, the patient's App is also configured to store, in a memory on a patient's smart device, health-related information under the "My Health History" section/tab for the patient, such information including lists of the patient's past and current medical problems (e.g., hypertension, hypothyroidism, arthritis, ulcerative colitis), previous surgeries (e.g., appendectomy), allergies (e.g., medication allergies such as to penicillin and codeine), and prescription and over-the-counter medications previously or current taken (the over-the-counter medications may also be under a separate tab "My Medications" on a main icon screen per FIGS. 4 and 23). The patient or another person can enter this information into the patient's App via a data-input screen that the App causes the patient's smart device to display, the App can store the information in memory onboard the smart device, and, thereafter, the patient or a designated person can access the information via the patient's or the other person's App.

Figure 29:
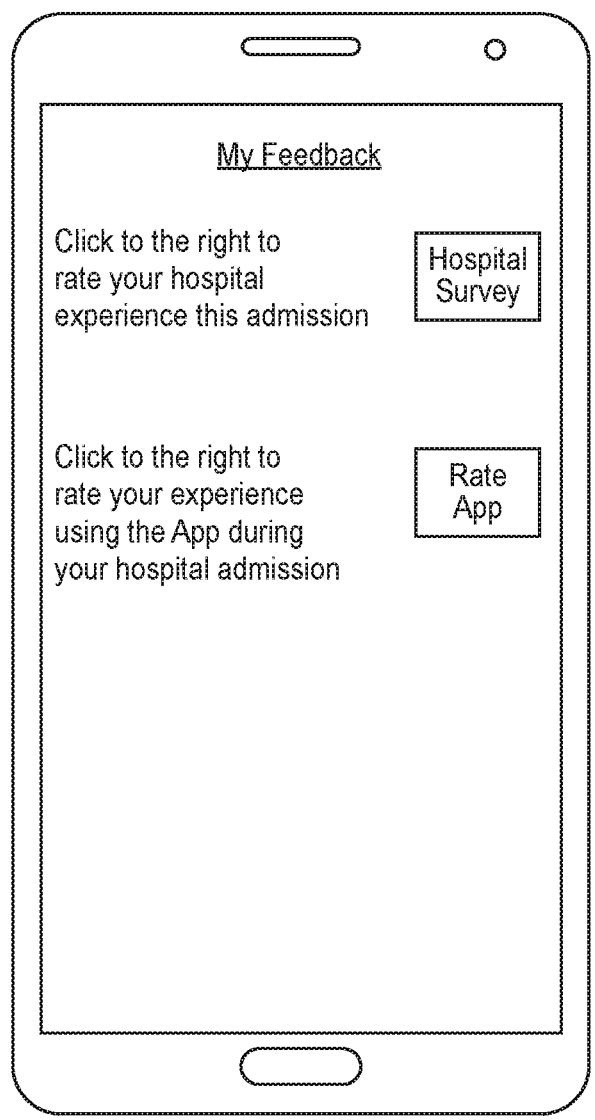
FIG. 29 is a screen view of an electronic device that is configured to execute one or more instructions of a medical-stay-related software application, and to display, in response to the executed one or more instructions, a feedback menu that allows a patient to submit a satisfaction survey re the medical facility or the software application, according to an embodiment.
Figure 30:
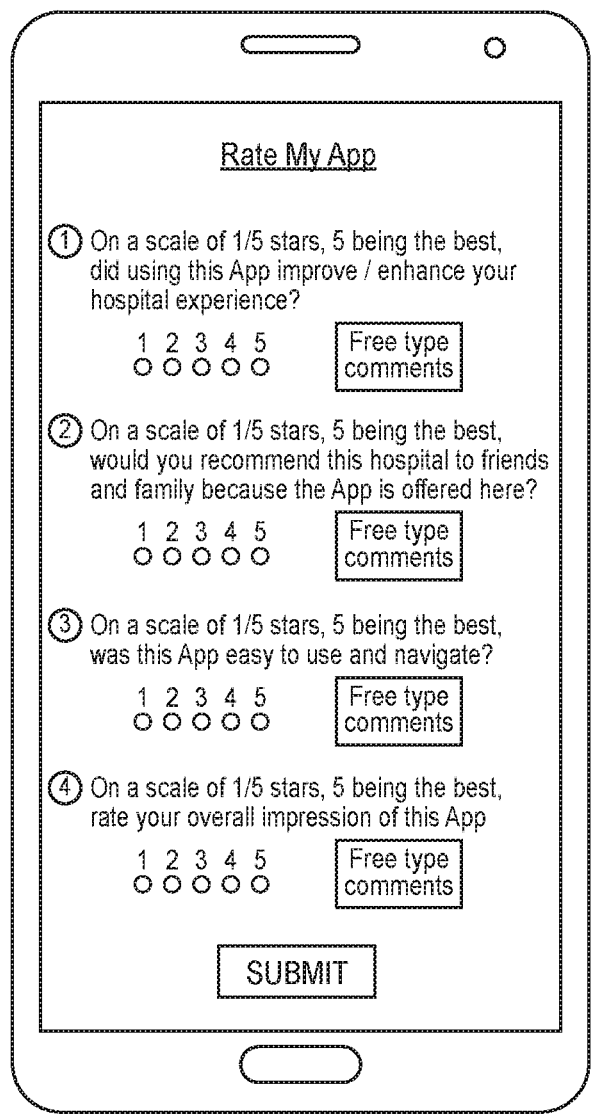
FIG. 30 is a screen view of an electronic device that is configured to execute one or more instructions of a medical-stay-related software application, and to display, in response to the executed one or more instructions, a survey that allows a patient to rate the software application, according to an embodiment.

Referring to FIGS. 4 and 29-30, in an embodiment, the App is configured to display hypertext links to patient-satisfaction surveys. The patient can rate his/her experiences directly via a display screen that the App causes the smart device (on which the App is installed) to generate and to display. For example, a patient may be more likely to submit a survey electronically than he/she would be to submit a paper survey mailed to him/her after his/her hospitalization or other medical treatment. The App is configured to send the survey information to the hospital administration (or to the administration of another treating facility), which can then use this information to help improve the experiences of patients, family members, and friends.

Although physician participation would facilitate wide acceptance and adoption of the App, physician participation with any new piece of equipment or tool can be challenging to obtain.

Therefore, in an embodiment, the App is configured to achieve a goal of improving both patients' and physicians' experiences without increasing physician workload. A physician's App can be configured so that its functionality requires little more from the physician other than touching, clicking, or otherwise selecting an "R" button in the physician's App next to the patient's name to send an alert to the patient and his/her family and friends, via their respective Apps, that the physician anticipates rounding on the patient in a next time period, e.g., within the next 60 minutes. Although not all physicians may buy into utilizing the App, even if some physicians, such as Hospitalists (who in many cases are employees of the hospital), caring for hospitalized patients utilize the App's functionality, the patient experience is likely to be improved. The App also can be configured for easy use by other medical professionals such as Nurses, Unit Clerks, PCAs (Patient Care Assistants), Physical Therapists, members of a Radiology Department, members of a Surgery Department, Social Workers, Case Managers, and other members of a patient's healthcare team.

A patient's App can be configured for utilization not only by an inpatient (e.g., a patient staying at a hospital or other medical facility), but by an outpatient, such as a patient undergoing outpatient surgery or other outpatient treatment. For example, a patient having outpatient surgery and each of his/her family and friends can utilize a respective App to receive information about the patient's Incision Time and Time of Arrival to PACU (Post Anesthesia Care Unit). Accordingly, an outpatient, his/her family, and his/her friends can gain exposure to the benefits of the App, and, in the future, are more likely to decide to utilize the same hospital or other treatment facility for their inpatient care as well as their outpatient care.

Both a patient and his/her physicians can configure their respective Apps in a way that can improve, dramatically, the patient's experience with his/her medical treatment, whether the treatment is on an outpatient or inpatient basis. Therefore, if patients begin to utilize the App and see how much it improves, for example, their hospital experiences, then support and use of the App by a hospital or other medical-treatment facility can be an immense draw for patients to seek outpatient and inpatient treatment at the hospital or other medical-treatment facility.

Narrative of App Functionality—How the App Works (e.g., How a Smart Device Functions and Operates while Executing Instructions that Form the App)

For clarity, configuration and operation of the App for patients and others is described below according to an embodiment, and differences between the patient, family-friend, and physician/other-healthcare-provider configurations of the App are described as appropriate. Where no such difference is described, it is understood that the family-friend, physician, and any other configurations of the App operate in a manner similar to the patient configuration of the App. For purposes of example, the patient is described as being an inpatient in a hospital, it being understood that the App can be configured, and can function, similarly for another type of patient, such as an outpatient or a patient recuperating at home. Furthermore, although functions and operations may be described as being performed by the App, it is understood that a computing device, such as a smart phone, tablet, laptop, and desktop, perform the functions and operations in response to executing program instructions of the App.

Referring to FIG. 1, the App opens with a title screen or page with the name of the App and the App logo, and the device on which the App is installed displays the title page for a programmed, or otherwise set time, such as, e.g., 3 seconds.

Figure 37:
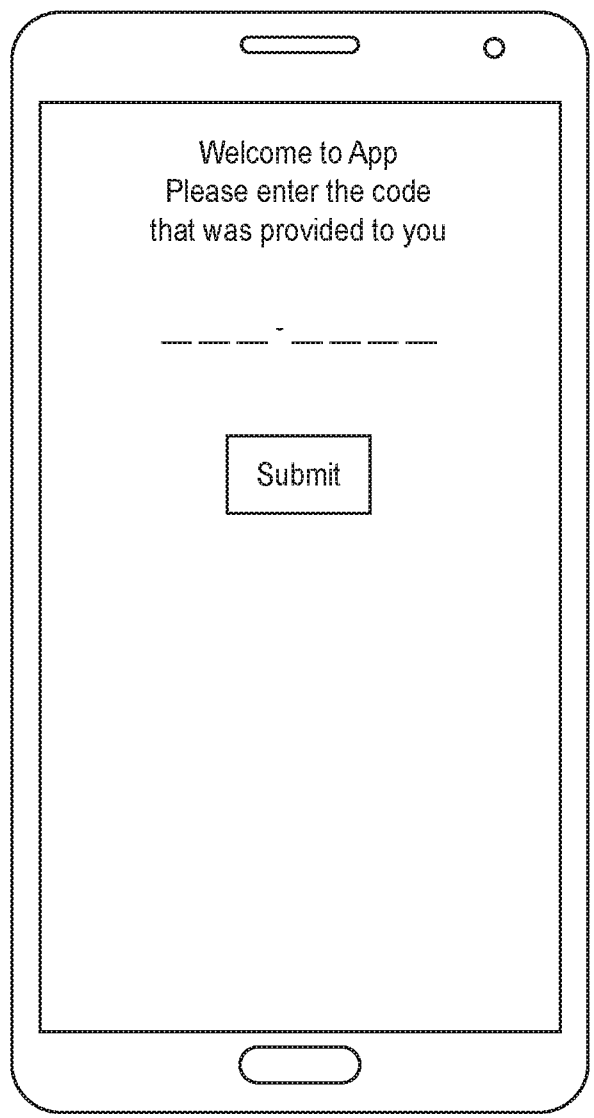
FIG. 37 is a screen view of an electronic device that is configured to execute one or more instructions of a medical-stay-related software application, and to display, in response to the executed one or more instructions, a page via which a person whom a patient authorizes to access the patient's medical-stay-related information can submit credentials to gain access to the information, according to an embodiment.

Referring to FIG. 2, in an embodiment in which the patient is admitted to a hospital, the App then automatically transitions from the App title page to a medical-facility title page for the medical facility (e.g., hospital) at which the patient is staying, and displays a greeting such as "Welcome to Hospital X." Using GPS locator technology of the smart phone (or other smart device) on which the App is installed, the App automatically loads the geographical location of, and information regarding, the hospital facility to which the patient is admitted. For example, the App automatically loads and syncs with the appropriate hospital by using services of the smart device provided by, or otherwise related to, the GPS locator. Underneath that greeting is a button or link "How to use this app." Pushing this button or link links to a URL at which is a hosted video that tutors the patient, family member, or friend how to use the App. Upon completion of the video, the App presents an option to skip loading the video tutorial screen, which follows the video, and to proceed directly to the log-in page (FIGS. 2-3, or to the App's Home Screen, FIG. 4, if the user has already logged in). A link to the video tutorial is still available on the Home Screen if the patient or other user would like to view the tutorial video again, and would like to access the video tutorial screen. After watching the video tutorial and possibly loading and viewing the tutorial screen, the App transitions to a page (not shown in FIG. 2) to identify a type of user such as "patient," "family member," or "healthcare professional." If the user is a patient, then he/she enters identifying data to access his/her information and to configure the App for a patient. After the App confirms the patient's identity, e.g., by contacting and receiving confirmation from a hospital server, then the App transitions to the patient Home Screen (FIG. 4). If the user is a family member or friend, then after he/she enters identifying information (e.g., name, phone number) and the App confirms the family member's or friend's identity, the App transitions to the family-friend Home Screen (FIG. 37). The App is configured to confirm the family member's or friend's identity, for example, by sending a confirmation request to the patient via e-mail, text, or the patient's App, and receiving, e.g., by the family member or friend manually entering it, a confirmation code sent by the patient's smart device upon approving the request. The patient's smart device may send the confirmation code to the family member or friend via text, email, facsimile, or another other suitable means. If the user is a physician or other healthcare provider, then he/she enters identifying data to configure the App for a healthcare provider (the configurations can be different for different healthcare providers). Once the App confirms the physician's (or other healthcare provider's) identity, e.g., by contacting a hospital server, then the App transitions to the healthcare provider Home Screen (FIG. 14).

The top of the patient Home Screen (FIG. 38) displays, e.g., the patient name, date of birth, medical record number, and room number (not shown in FIG. 4). The patient Home Screen also can display, at the top of the page, the patient's current location from choices such as "In Room," "In Surgery," "In Recovery," and "In Study". The patient's Home Screen also can display a number, e.g., twelve, displayed icons for the patient to choose from; each icon, when "pressed" or otherwise selected (e.g., by touching a portion of a touch screen located over the icon), takes the patient to a respective screen that displays the information described by the icon. The following are examples and accompanying descriptions of such icons.

My Doctors Icon

Referring to FIGS. 4 and 7-8, and 38 when selected/pressed, the "My Doctors" icon lists, for the patient, all the physicians and other healthcare professionals taking care of the patient during his/her hospitalization. The App is configured to "pull" this information from the patient's electronic medical record (EMR) on a hospital server. The patient's smart device on which the App is installed communicates with the hospital server, for example, via a wireless router at the hospital, or via a cellular network. At the top of the list is the patient's primary physician. This is the physician that is the admitting physician and typically will be the primary physician responsible for the care of the patient. Below the primary-physician designation is a list of other doctors. These are the consulting physicians involved with the care of the patient. Under each physician name is the practice area or type of physician (e.g., Nephrologist, Cardiologist) and a biography "button" that the patient can press for further information such as a short bio of the physician. The patient (or family member or friend using the App) can "click" on physician type, and the App will display a brief explanation of what that type of physician that physician is, and the medical problems and other issues that this type of physician manages. The biography can list, for example, where the physician went to medical school and where he/she did his/her residency and fellowships. Also, the biography can include a list of any partners, physician assistants, nurse practitioners, and resident physicians that may cover for/work with the physician. The biography can also include the physician's office address and phone number, and a photo of the physician so that the patient and his/her family and friends will know what the physician looks like. Because a patient can be seen by several physicians each day, even with the photos it can be confusing for the patient and the family members and friends to keep track of whom the patient has already seen in a given day. Therefore, under the My Doctors icon there also can be a list of the physicians that the patient has seen today. As each physician sees the patient, his/her name will automatically populate this list. This can be achieved, for example, by the physician indicating, via the physician's App, that he/she has seen the patient, and the smart phone on which the physician's App is installed notifying the hospital server, which provides this information to the smart phone on which the patient's App is installed via, for example, a wireless or cellular network. Or, the physician's smart phone can provide this information directly to the patient's smart phone via, for example, a wireless or cellular network.

Care Team Icon

Referring to FIGS. 4, 16, and 17, when a patient clicks on the My Care Team icon in the patient's App, the App takes the patient to the My Care Team Page, which has separate buttons for nurses, patient-care assistants, case managers, therapists, and other categories of healthcare professionals on the patient's care team. In an embodiment, only the categories that include at least one professional who is involved in the patient's care will have a corresponding button. If, for example, the patient does not require therapy or does not have a Case Manager assigned to him/her, then the patient's App omits buttons corresponding to the therapy and case-manager categories. Further in example, when the patient clicks on the My Nurse button, the names of the nurses on the patient's healthcare team, and their photos, will appear on the page, as well as the respective hours during which the nurses will be involved in the patient's care. There also will be, on the page, a written explanation of the nurses' roles in the patient's care. Pressing the My PCA (patient-care-assistants) button provides similar information for the patient-care assistants, and pressing the My Case Manager button causes the patient's App to list the name of the case manager with his/her photo. Further in example, the responsibilities of the case manager are also listed, and when planning for discharging the patient to another facility (e.g., a rehabilitation center), the case manager is able to send, to the patient, family members, and friends via the case manager's App, links to various facilities that take the patient's insurance. This feature allows a patient and his/her family and friends to better research and choose a facility to which the patient would like to be transferred (for example, if the patient's care involves transferring him/her from a hospital to another facility such as a rehabilitation facility). Further in example, in response to the patient pressing the My Physical Therapist displayed button, the patient's App lists the names of the patient's assigned physical therapists with their photos and displays an explanation of what a physical therapist does. Using his/her App, a physical therapist can send to the patient's App links for exercises and other rehabilitation handouts so that the patient can continue physical therapy exercises and other rehabilitation after the patient is discharged and is home.

My Diagnosis Icon

Figure 31:
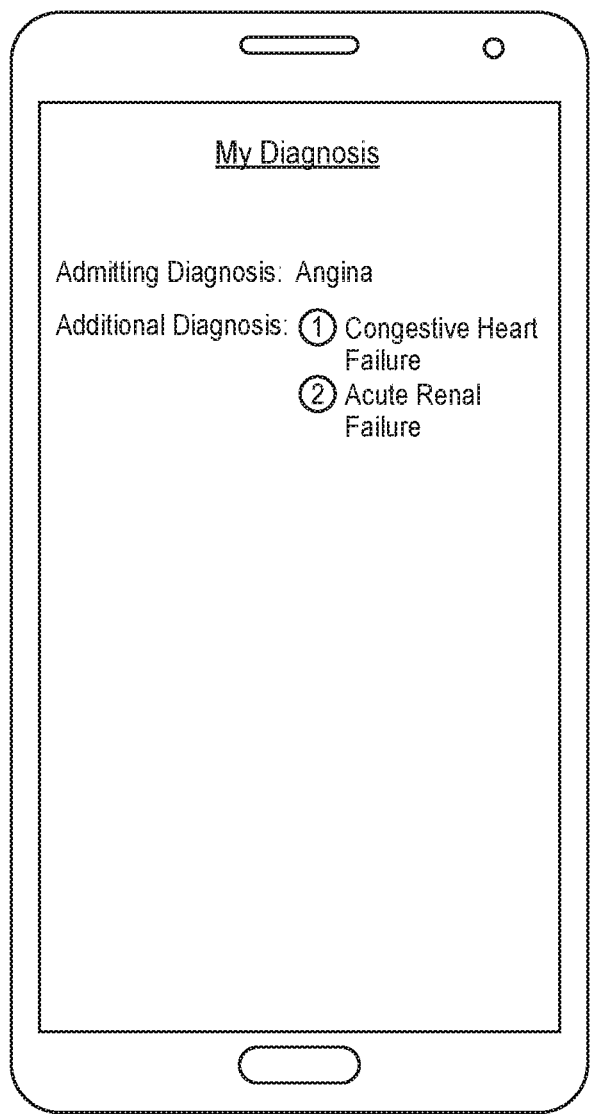
FIG. 31 is a screen view of an electronic device that is configured to execute one or more instructions of a medical-stay-related software application, and to display, in response to the executed one or more instructions, a patient's medical diagnoses determined during the patient's medical stay, according to an embodiment.

Referring to FIGS. 4 and 31, pressing the displayed My Diagnosis button in a patient's App lists the admitting diagnoses for the patient's inpatient admission (e.g., the symptoms and confirmed maladies for which the patient was admitted for treatment, and any symptoms and maladies confirmed after admission but during the stay); examples of such diagnoses include pneumonia and chest pain. The patient's App can download the diagnoses information from, for example, the Electronic Medical Record (EMR) admitting orders, which are typically stored in a database on a hospital server.

My Questions Icon

Referring to FIGS. 4 and 9, pressing the My Questions button in a patient's, family member's, or friend's App causes the App to display a page in which the user can type in questions to ask the patient's physicians or other members of the patient's care team. For example, on the left side of the page, each question is numbered, and on the right side of the page next to the question are one or more boxes. Under the question is a spot for the physician, or other care-team member, to type or to dictate a response. Any family and friends who have been invited by the patient also can post questions for the care team and can see the response(s) to all questions, or to questions selected (e.g., via the same page as shown in FIG. 9) by the patient for publishing to the Apps of family members and friends. When the patient's, family member's, or friend's question has been answered, he/she can check the respective box on the right-hand side of the screen to denote the question as "answered". The page also can include a box for notes, which the question asker or the question answerer can write.

My Schedule Icon

Figure 12:
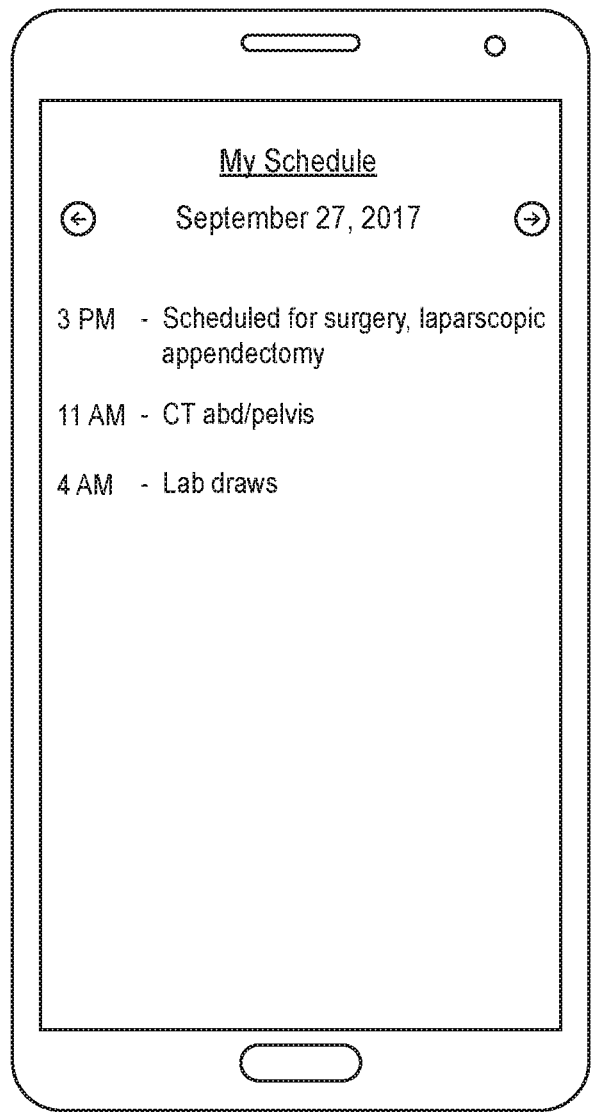
FIG. 12 is a screen view of an electronic device that is configured to execute one or more instructions of a medical-stay-related software application, and to display, in response to the executed one or more instructions, a page listing a patient's medical schedule for the included date, according to an embodiment.

Referring to FIGS. 4 and 12, in response to pressing the My Schedule button, the patient's App causes the smart device on which the App is installed to display the patient's healthcare-related daily schedule sorted by date; alternatively, the App causes the smart device to display only the current day's schedule. For example, the current date is listed first at the top of the screen. Example events that are included in the displayed schedule include surgeries, imaging studies, therapy sessions, and meals. The patient can click on, for example, the image-study event (e.g., the CT abd/pelvis event in FIG. 12) and, in response, the patient's App causes the smart device to generate and to display a brief explanation of the study so that the patient will have some idea of what to expect from undergoing the study.

Invite Family and Friends Icon

Referring to FIGS. 4-6, in response to a patient clicking on the Invite Family and Friends button FIG. 4, the patient's App causes the smart device on which it is installed to generate and to display a pop up that asks the patient for authorization so that the App can access the patient's contacts stored on his/her smart device (e.g., smart phone), in conjunction with, e.g., a phone or e-mail application (e.g., Microsoft Outlook®, Google Mail®). From the patient's contact list, the patient can choose which family members and friends to whom he/she would like to grant access to the patient's information via the App. The patient's App then causes the patient's smart device to contact (e.g., by e-mail or text) each authorized family member and friend and invites him/her to download the App and to install the App on his/her smart phone or other smart device. For each authorized family member and friend who downloads the App, they also are assigned a specific PIN number to complete the log in and access the information in the patient's App (see FIG. 37). The patient's smart device will communicate each of the pins to a respective one of the invited family and friends via text, email, or other suitably secure technique. The family member's or friend's App then sends, upon entering the PIN, a message to the patient's smart device so the patient may confirm the family member or friend should have access to the information in their App; in response to the submission of the PIN, the patient's App allows the patient to accept the invitee to give the family member or friend access to view a selected portion of, or all the information, in the patient's App, such as the My Doctors, My Care Team, My Diagnosis, My Questions, My Schedule, My Goals, My Alerts, My History, and My Meds icons. Furthermore, in an embodiment, even after becoming authorized, a family member or a friend cannot grant other people access to use the App to access the patient's information; only the patient can authorize others to access his/her information via the App. Alternatively, the patient's App can be configured to allow the patient to authorize certain others (e.g., the patient's parents or spouse) to grant others access to the patient's information via the App.

My Alerts Icon

Figure 10:
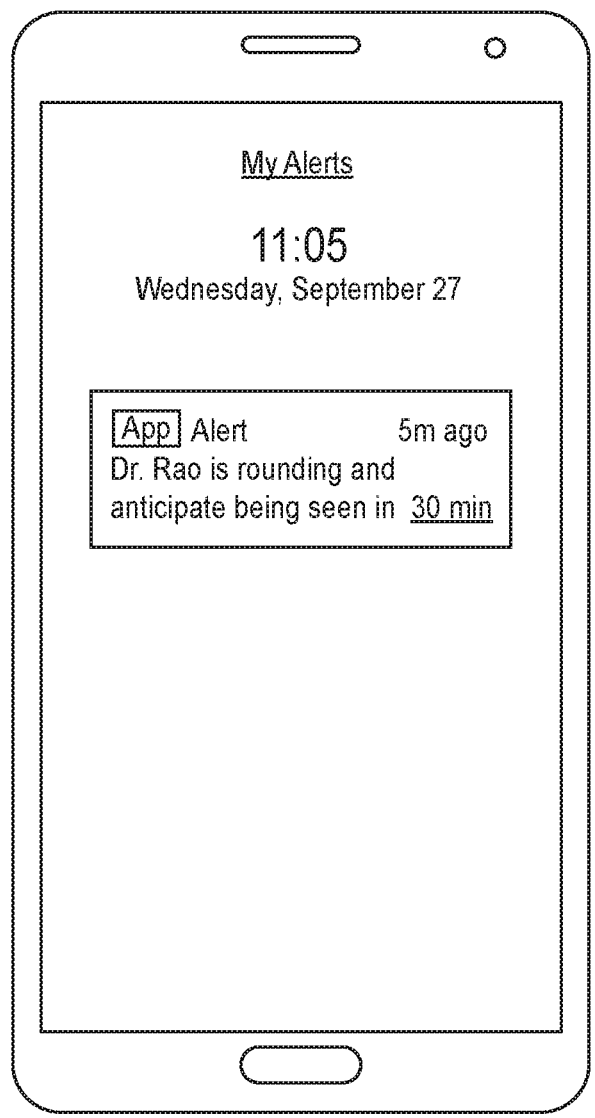
FIG. 10 is a screen view of an electronic device that is configured to execute one or more instructions of a medical-stay-related software application, and to display, in response to the executed one or more instructions, a page that provides alerts to the patient, according to an embodiment.
Figure 11:
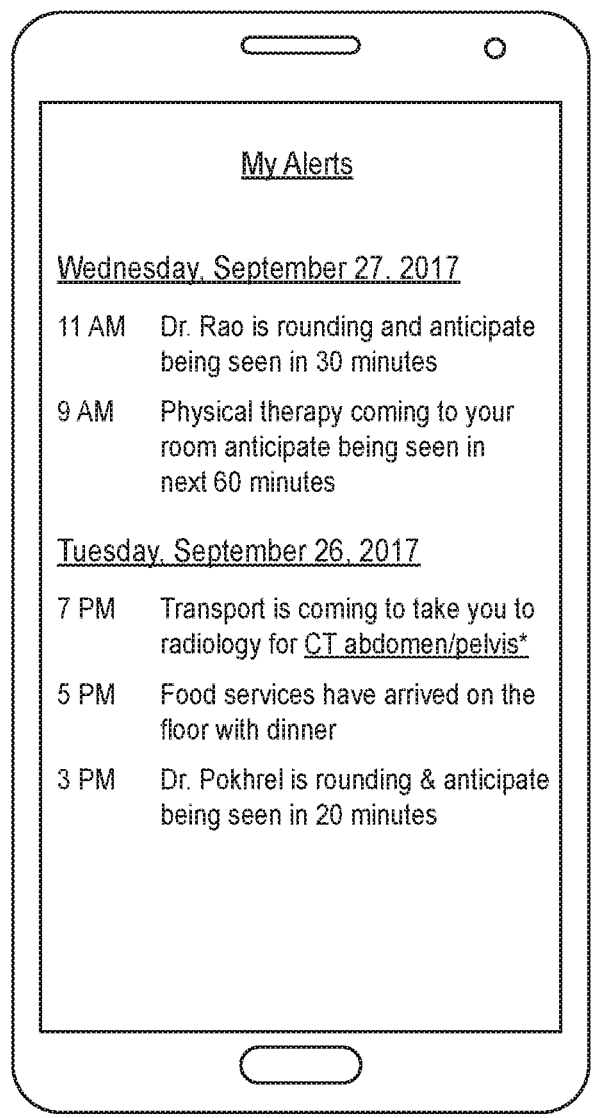
FIG. 11 is a screen view of an electronic device that is configured to execute one or more instructions of a medical-stay-related software application, and to display, in response to the executed one or more instructions, a page that includes a list of alerts, according to an embodiment.

Referring to FIGS. 4, 10, and 11, pressing the My Alerts button causes the patient's App to cause the smart device on which the App is installed to generate and to display alerts sorted by day with the current-day's alerts listed, for example, at the top of the smart-phone screen; alternatively, the smart device may display only alerts for the current day. Each of the patient's, family members', and friends' Apps can be configured to cause an alert to "pop up" on the respective user's smart device, regardless of whether the App is "open" on the device, and the popped-up alert remains until the patient selects "ok," or takes some other action to acknowledge the alert. That is, the App can run "in the background" to generate alerts even when the App is inactive. During the hours, for example, of 7 AM-7 PM, the App is configured to cause the smart phone (or other smart device) to generate, for example, an audio alert (e.g., a pleasant sound) in addition to the text alert. In contrast, during the hours, for example, of 7 PM-7 AM, the App is configured to cause the smart phone to issue only silent text alerts. The App is further configured to generate alerts for events such as a doctor of the patient is rounding, and the alert can include a scheduled or estimated time at which the event is to occur. For example, the alert can read "Dr. X is rounding and you can anticipate being seen in the next 30 minutes." Examples of other alerts include "Lunch trays have arrived on the floor and will be delivered to your room shortly." Members of the healthcare team, such as patient transport, can send, via their, or their departments', Apps, an alert, such as an alert notifying the patient that transport will be coming to take the patient for, e.g., an imaging study or to go to surgery. Other members of the healthcare team that are authorized to send visitation alerts to the patient's App via their, or their departments', App include case managers and therapists. Also, under the My Alerts icon, the patient's App on the smart device on which the App is installed can be configured to generate, and to display, a running list of the alerts that the patient received during a given day, with the most recent alert listed, for example, at the top of the screen. The patient's App also can be configured to generate an alert in response to a respective scheduled event listed under the My Schedule icon (see FIGS. 4, 12, and 13).

My Goals Icon

Referring to FIGS. 21 and 22, in response to the pressing of the My Goals button (e.g., FIG. 4), the patient's App causes the smart device on which the App is installed to display a list of patient goals (FIG. 21) that are set, for example, by one or more members of the patient's healthcare team, such as a nurse, via a team member's intranet version of the app (FIG. 22). The team member's App is configured to display a "pick list" of goals that the team member (e.g., a nurse or physical therapist), can add to the patient's list of goals. For example, healthcare professionals often encourage a patient in the hospital to walk to prevent Deep Vein Thrombosis (DVT). The patient's App can be configured to cause the patient's smart device to function, for example, as a pedometer to keep track of the patient's walking distance. The goal information can be made visible to all members of the patient's healthcare team and family and friends via the members' Apps. Another example of a patient goal is for the patient to use an incentive spirometer (IS), which is a device designed to encourage patients to expand their lungs to prevent atelectasis and pneumonia while the patient is in the hospital. For example, the patient's App is configured to cause the patient's smart device to generate an alert every hour reminding the patient to use the incentive spirometer if a member of the patient's healthcare team chooses strict hourly IS as a goal for the patient. The incentive spirometer is an order that typically is stored in a database as part of the patient's EMR (electronic medical record), and the patient's App accesses the EMR to determine if an order exists for the patient to use a spirometer. If such an order exists, then the patient's App adds the IS to the patient's list of goals. Examples of other patient goals include transition from intravenous pain medications to oral pain medications, tolerating a general diet, returning to normal bowel function, and regaining the ability to urinate.

My Medical History Icon

Referring to FIGS. 4 and 25-28, in response to the pressing of the My Medical History button or icon on the App icon page (FIG. 4), the patient's App causes the patient's smart device on which the App is installed to list, for example, the patient's medical problems, previous surgeries, current home medications, and allergies. The patient's App can cause the patient's smart device to pull from the hospital's EMR all of the ICD 10 (International Classification of Disease) codes and relevant CPT (Current Procedural Terminology) codes from the patient's admission. The patient also can add to his/her medical problems and surgeries from a pick list of common diagnoses, common surgeries, and common allergies that the App causes the patient's smart device to display. Allergies are also listed in the EMR, and, therefore, the patient's App can cause the patient's smart device to pull the patient's allergy information from the EMR to populate the required information in the My History section. The patient can configure his/her App to retain this personal health information in the App even after the patient's hospital stay is completed. For example, the patient can add to, and access, this information for use at outpatient appointments. In an embodiment, after a configurable or set period of time, e.g., 1 month, from patient discharge, a significant amount of information contained in the patient's App will automatically delete (e.g., alerts, questions, schedule, doctors), but the information under the My History tab of the patient's App can be configured to remain, and to be available, for a longer period of time, or permanently. The patient's App also can be configured to display, under the My History icon, a list of all of the patient's current home medications. The patient's App can be configured to pull, from the medical reconciliation portion of the EMR, a list of the patient's home medications. When a patient is admitted to the hospital, a pharmacist or a nurse reviews all of the patient's home medications and dosages to insure accuracy, and the inputs those medications into the EMR. At the time of discharge of the patient, the patient's App imports a list of discharge medications from the EMR. Frequently after an inpatient hospitalization, a patient's list of discharge medications differs from the list of medications that the patient was taking prior to his/her hospitalization. The patient's App can be configured to store a current list of medications in a memory of the smart device on which the patient's App is installed. In an embodiment, the patient's App is configured to help the patient to keep track of a current list of his/her home medications on a continuing basis. When a patient's medications change, the patient can edit the list of current medications via the App to reflect the changes. For example, under the My Medical History icon, a patient can select "add a medication" and input a new medication, or "edit a medication" to, for example, change a dose, or "delete a medication" to remove a medication that he/she is no longer taking. Alternately, a third party, such as the patient's pharmacy, may be granted access to the patient's smart device via the App such that the pharmacy can maintain the medication list up to date.

My Discharge Icon

Referring to FIGS. 4, 32, and 38, in response to the pressing of the My Discharge button or icon (FIG. 38) displayed on the patient's smart device, the patient's App causes the smart device to display a list of the physicians and other healthcare professionals with whom the patient is to schedule follow-up appointments after the patient's discharge. The patient's App also displays post-discharge instructions, including a post-treatment regimen, such as, for example, no weight bearing on right lower extremity. Under the My Discharge icon, the patient's App also displays, for example, the patient's discharge diet and any specialized instructions. In an embodiment, the patient can configure his/her App so that the hospital server will push, via the patient's App, a notification a period of time (e.g., one day) after the patient's discharge to remind the patient to schedule his/her follow-up appointments with the recommended physicians. And if, for example, the patient does not have a primary care physician (PCP) with whom the patient has already established a doctor-patient relationship, under the My Discharge icon the patient's App can be configured to list a phone number to help the patient establish care with a hospital-recommended PCP.

My Feedback Icon

Referring to FIGS. 4 and 29-30, in response to the pressing of the displayed My Feedback icon, the patient's App causes the smart device on which the App is installed to display, or otherwise to direct the patient to, a survey provided by the hospital for the patient to rate his/her hospital experience. In addition, or alternatively, the patient's App causes the smart device to display, or otherwise to direct the patient to, a survey provided by the App's developer for the patient to rate his/her experience with the App. The Apps of family members and friends, can include or provide a similar My Feedback icon, which allows family members and friends, also to rate the hospital and the App.

Hospital Information Icon

Figure 33:
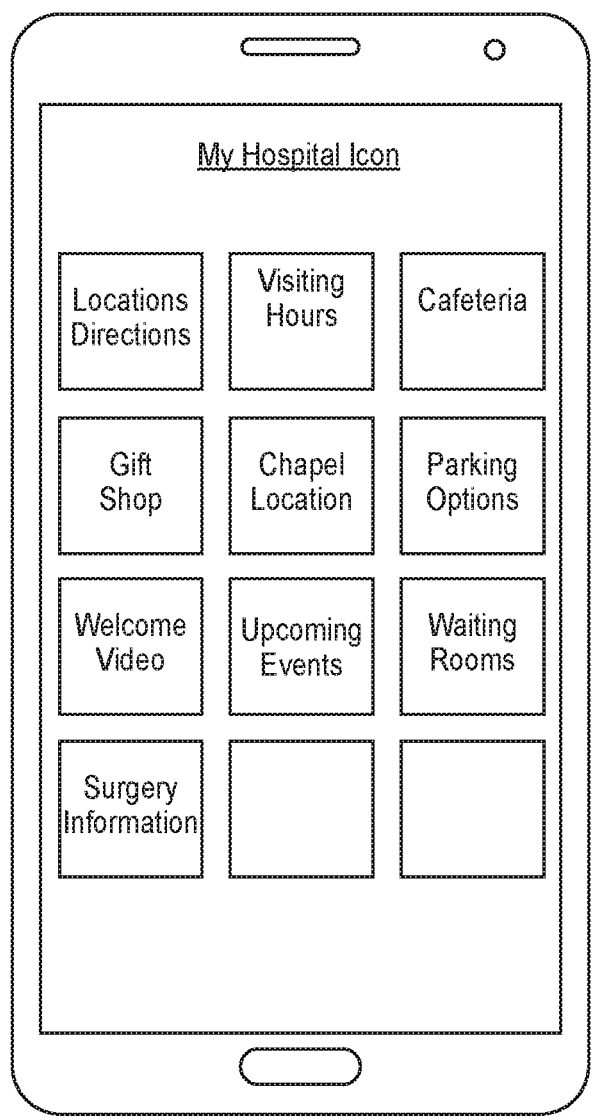
FIG. 33 is a screen view of an electronic device that is configured to execute one or more instructions of a medicalstay-related software application, and to display, in response to the executed one or more instructions, information about a medical facility where a patient is staying, according to an embodiment.

Referring to FIGS. 4 and 33, in response to the selection of the My Hospital icon, the patient's App is configured to provide the patient important, general hospital-related information, including, but not limited to, visiting hours and the hospital's visiting-hour policy, cafeteria hours and locations, locations of the different waiting rooms in the hospital, chapel hours and location, gift shop hours and location, and parking options/information. Under the My Hospital icon, the patient's App also provides a map of the hospital floors, and a video tour or tutorial of the hospital. And the Apps of family members and friends can be configured to provide, under a respective Hospital Information icon (not shown in FIGS. 4 and 33), similar information to the smart devices on which are installed the Apps for authorized family members and friends.

The above description is of an embodiment of the structure and functionality of the App configured for use by a patient, i.e., of the functionality of the App from the patient's perspective, unless otherwise noted.

Below is described an embodiment of the structure and functionality of the App configured for use by a healthcare provider such as a physician, i.e., of the functionality of the App from a doctor's perspective, unless otherwise noted. Although the App configured for use by a doctor is generally described, it is understood that the description can apply to a healthcare professional (e.g., a nurse, case worker, medical technician, administrative staff) other than a doctor.

From a provider's (e.g., nurse or doctor/physician in this example) point of view (i.e., an App configured for use by a healthcare provider), there are at least two mechanisms with which to interact with the Apps of patients, family members, and friends. A doctor can install the App on his/her smart device (e.g., a smart phone), and can configure the App for a healthcare provider. The App, or a companion application such as a computer Intranet Based Program, can be installed on a computer or server (e.g., a hospital computer or server) that healthcare professionals and their clerks can log into to input information that the computer or server is configured to upload to the Apps of a patient, family members, and friends; for example, the computer or server can push, automatically, some of the relevant information for the patient, family members, and friends from the EMR to the patient's, family members', and friends' Apps. Much of the communication from the computer or server will automatically be uploaded to the patient's, family members', and friends' Apps due to the ability of the computer or server to interface with the hospital's electronic medical records. For example, information such as the patient's primary physician, patient allergies, and home medications, can be drawn directly from the EMR, which may already store this information; therefore, such automatic upload eliminates the needs for a clerk, healthcare professional, or other human operator to manually upload this information to the patient's, family members', and friends' Apps.

The healthcare provider's App, henceforth described as Provider's Smart Phone App, starts by displaying a login screen. For example, a doctor can log in with a username and password, or he/she can more quickly login in the future after setting up his/her Provider Smart Phone App, using a fingerprint (this depends on whether the smart phone on which the App is installed has fingerprint-detection capability). The first time the doctor opens the Provider's Smart Phone App, the App takes him/her to a set-up page, where he/she inputs his/her name. The doctor also can also view a provider tutorial that explains how to use the Provider's Smart Phone App.

After the set-up is complete, the Provider's Smart Phone App takes the doctor to his/her Home Screen. After the initial set up, the Provider's Smart Phone App takes the doctor to the Home Screen upon a successful login. The top of the Home Screen displays the heading "My Patients."

Referring to FIGS. 14-15 and 34-36, under the My Patients icon (e.g., after pressing the displayed My Patients button on a doctor's home screen) is a list of all the patients assigned to the doctor. The provider's App can organize the list of patients by patient floor/location, or alphabetically, and the doctor can choose this organizational preference by pressing a "My Preferences" Icon on the Home Screen. In addition to the patient's name, the provider's smart phone App is configured to list the patient's room number (or other location identifier). Across from the patient's name and room number, on the right-hand side of the screen, are displayed two buttons. One button is labeled "Send Rounding Alert" and the other button is labeled "Patient Seen." In response to the doctor selecting "Send Rounding Alert," the provider's App sends an alert to the patient via the patient's App that the doctor is coming to round (the provider's App also can send this alert to the Apps of family members and friends). The timing between the sending of the alert and when the doctor anticipates seeing the patient can be customized by the doctor in the "My Preferences" page of the provider's App. The doctor can select from a variety of times using a scroll bar, such times including, for example, "5 Min, 30 Min, 1 Hour, 2 Hours," etc. In response to the doctor sending the rounding alert, the patient receives an alert such as "Dr. X is rounding and you can anticipate being seen in the next 30 minutes;" as stated above, this notification also can go to authorized family members and friends directly via their Apps. The currently selected timing listed in the rounding alert is noted above a displayed button "Send Rounding Alert," so the doctor can easily see what he/she has set as the current timing for the rounding alert. In response to the doctor pushing the "Patient Seen" button after seeing the patient, the doctor's App notifies the patient's App such that in the patient's App under the "My Doctors" tab, the doctor will be listed under the heading "Doctors I Have Seen Today."

At the bottom of the home screen (FIG. 14) displayed by the provider's smart device while executing the provider's App, under the list of the doctor's patients, there are displayed several buttons, including, but not limited to, "Add a Patient," "Remove a Patient," "My Preferences," "View Tutorial," and "Help/Support."

The "Add a Patient" button allows a doctor to add a patient to his/her list of patients kept by the provider's App. The doctor's App allows the doctor to search for a patient to add to his/her list of patients by last name or by floor, for example (the list of patients to be searched may be stored on the doctor's smart device, or on a hospital data base with which the doctor's smart device is in communication). The doctor's App also can add, automatically, a patient to a doctor's list of patients in response to the placing of an order in the EMR for the doctor to be a consultant in the patient's care, and the doctor's App also can add, automatically, the doctor's name to the patient's My Doctors Icon under the "My Consulting Doctors" tab of the patient's App. In response to a doctor placing admitting orders, the doctor's App automatically names that doctor "Primary Physician" on the patient's App, and adds the patient's name to the doctor's list of patients in the provider's App. The doctor's App is configured to address complexities that arise with frequent hand-offs of patients. For example, the hospitalist doctor that takes care of the patient may change on a day-to-day basis. At, for example, 0300 hours, the doctor's App automatically deletes the patient's name from the provider's App list in the App of any doctor who is denoted as a "Hospitalist." Also, the patient's App automatically deletes from the patient's list of doctors, at approximately the same time (e.g., 0300 hours), any doctors denoted as a "Hospitalist." And each day when the Hospitalist Service for the hospital assigns patients for rounding to each hospitalist doctor, the Hospitalist service also inputs the doctor's assigned patients into the hospital's App (e.g., installed on the hospital's server as an Intranet version of the App) so that the name of that day's Hospitalist assigned to the patient is automatically uploaded to the patient's App and the assigned hospitalist's App to make the name of the assigned hospitalist available to the patient in the list of the patient's doctors maintained by the patient's App installed on the patient's smart phone, and to make the name of the assigned patient available to the day's hospitalist in the doctor's App, such that the list of patients for the hospitalist is correct in the doctor's App, which list is accessible from the home screen under the displayed "My Patients."

Referring to FIG. 14, a "Remove Patient" button on the home page (or another page) of the provider's App allows a doctor to remove a patient from his/her list of patients. If a doctor saw a patient for several days but then elected to sign off because seeing the patient was no longer medically necessary, then the doctor could remove the patient from his/her list of patients on his/her App. When a patient is discharged from the hospital, the provider's App automatically receives this information from the EMR and automatically removes the patient from the doctor's list. Adding and removing patients on the provider's App does not change the information in the patient's App. Even after a doctor signs off on a patient and removes the patient from his/her list of patients on his/her provider's App, the doctor's information is still available on the patient's App so that the patient can remember what specialists/consultants saw him/her during his/her hospital stay. The patient's App can be configured such that only the hospital's App can edit the physician list or other data in under the My Doctors icon of the patient's App. Such a configuration lessens the chances of the patient, or another person, accidentally deleting or otherwise altering this information.

Referring to FIGS. 14-15, on the "My Preferences" page of the provider's App, the doctor can edit the parameters of his/her App to suit his/her individual needs. For example, there is a menu via which the doctor can select, or otherwise edit, the timing of the rounding alert (the time between sending the alert and the time that the doctor anticipates seeing the patient). For example, there is a scroll bar where the doctor can choose from a variety of times from, e.g., 5 minutes to 2 hours. Under this section, the doctor also can organize his/her list of "My Patients" by, for example, choosing to list the patients by floor/location, or alphabetically. On the "My Preference" screen there is a button that reads "View My Bio." A physician can view the Bio about him/her that is available to the patient on the patient's App (and is available to family members and friends on their Apps) to confirm all the information is correct. If there is a problem with the doctor's bio on the patient's App, for example the doctor's office number is incorrect, there is a place on the page for the doctor to submit a request to edit his/her bio.

Referring to FIG. 14, pressing the "App Use Instructional Video" button causes the provider's App to render or re-render a tutorial describing how to configure the App for use by a doctor or other healthcare professional, and how to use the App so configured. The ability to re-render the tutorial allows a doctor or other healthcare professional to refresh his/her training in how to use the provider's App.

Pressing a "Help/Support" button (see FIG. 38 for a help/support button on the home screen of a patient's App) causes the doctor's App to generate a screen that displays contact information, such as a hypertext link, for an IT support technician. This feature can also be included in the Apps configured for use by patients, family members, friends, and intranet users.

Figure 34:
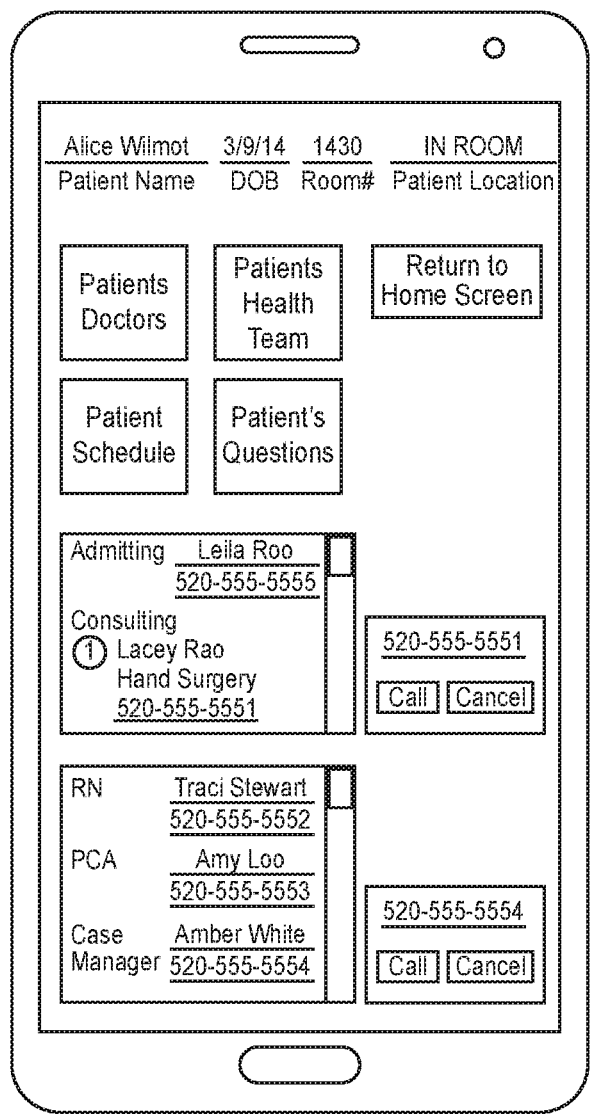
FIG. 34 is a screen view of an electronic device that is configured to execute one or more instructions of a medical-stay-related software application, and to display, in response to the executed one or more instructions, information about a patient available for the physician on their smart phone to help facilitate care of the patient, according to an embodiment.
Figure 35:
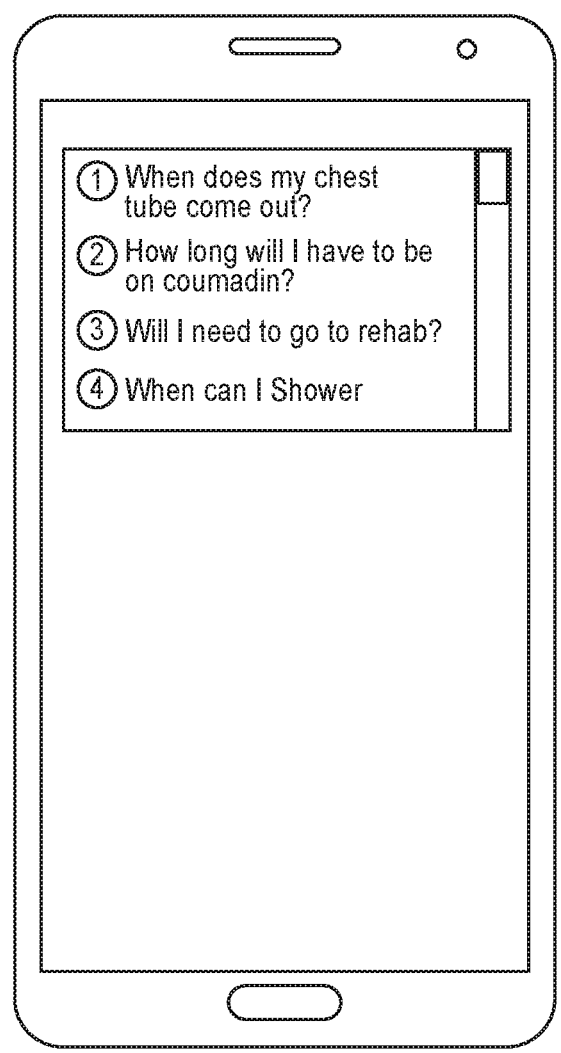
FIG. 35 is a screen view of an electronic device that is configured to execute one or more instructions of a medical-stay-related software application, and to display, in response to the executed one or more instructions, a page via which a physician on their smart phone application can review questions submitted by the patient to the medical-care team at a medical facility, according to an embodiment.

Referring to FIGS. 14 and 34-35, when a doctor clicks on a patient name in his/her list of My Patients on the home screen of the provider's App, the provider's App displays another screen that has more-detailed information about that individual patient. For example, at the top of the screen appears the patient's name, room number, and date of birth. Also, at the top of the screen, is an indicator of where the patient is currently located. Possible patient locations include Room, Surgery, and Imaging Study. Also, on this other screen are, for example, 4 buttons: Patient's Questions, Patient's Schedule, Patient's Doctors, and Patient's Healthcare Team. In response to the doctor clicking on Patient's Questions, the doctor's App displays the questions that the patient has listed in the patient's App under "My Questions." The doctor does not have to answer the questions, but there is functionality that allows the doctor to answer the questions, and to send the answers to the patient and anyone the patient has invited. For example, the doctor can type or dictate a response and send it to the patient's App. In response to the doctor clicking on "Patient's Schedule," the doctor's App displays any events that are listed in the patient's App under "My Schedule." For example, if the patient has an MRI scheduled at 10 am, or surgery scheduled for 3 pm, the doctor's App displays this information. In response to the doctor clicking on "Patient's Doctors," the doctor's App displays the primary/admitting physicians and the consultant physicians who are seeing the patient, including the doctor himself/herself. In response to the doctor clicking on "Patient's Healthcare Team," the doctor's App displays, e.g., the patient's nurse and Patient Care Assistant (PCA) so that the doctor knows the identities of the nurse and of the other team members who are currently caring for the patient. The doctor's App also can be configured to display photos of the nurse, PCA, and other healthcare-team members next to their names, respectively.

Another component of the functionality of a healthcare provider's App is an intranet-based application that interfaces with the EMR, and also allows input by clerks, nurses, etc., to populate the information that is displayed by the App in the different configurations of the App (e.g., the provider's App, the patient's App, the family's App, and the friend's App (there may be a single family-and-friends App instead of separate family and friend Apps). The intranet-based application may be part of, or separate from, one or more of the patient's App, the healthcare professional's App, and the friends-and-family App.

Figure 39:
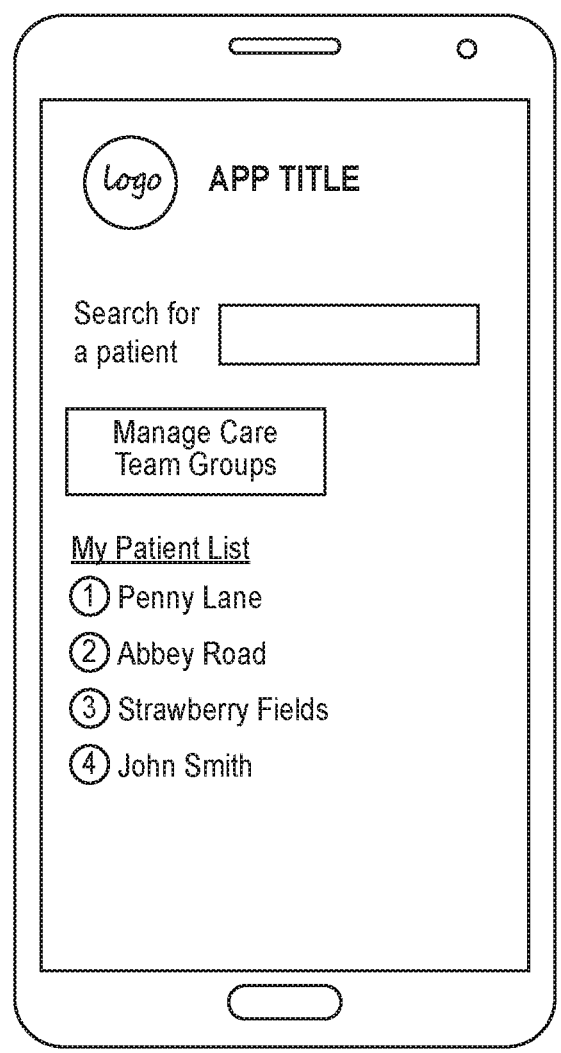
FIG. 39 is a screen view of an electronic device that is configured to execute one or more instructions of a medical-stay-related software application, and to display, in response to the executed one or more instructions, list of patients of a medical professional such as a nurse or physical therapist, according to an embodiment.

In an embodiment, referring to FIG. 39, the App, installed and configured for use on a device that is part of an intranet, is opened on a computer in the hospital, the computer being connected to a hospital-based intranet, and a user logs in with a user name and password. In response to logging in, the intranet App proceeds to a home screen. On the home screen, for example at the top, there is displayed a button for a search function "Search for a Patient" and a text box in which to enter the name of the patient to be searched. The intranet App effectively locates the patient by interfacing with the hospital's EMR.

Still referring to FIG. 39, also on the Home Screen is a button called "Manage Patient's Care Team" Or "Manage Care Team Groups."

When one (e.g., a clerk or charge nurse) clicks on "Manage Patient's Care Team" or "Manage Care Team Groups," the intranet App generates a screen via which he/she assigns groups of patients to a member of the care team. For example, once the upcoming day's nursing assignments have been designated, the clerk or charge nurse for that floor can use the intranet App to search by floor and to select all the patients that a nurse will be caring for, and then, after selecting the patient group, he/she has the option of assigning the patient group to a healthcare provider (e.g., a doctor). The intranet version of the App displays several types of providers to choose from (e.g., doctor, nurse, PCA, therapist, social worker/case manager). In an example, the clerk chooses "nurse" and assigns patients to the nurse. In response to the nurse logging into the nurse's App, the nurse's App generates a home screen having, at the bottom, "My Patient List." In this screen is also where a user can update, e.g., daily, a hospitalist doctor's patient assignments, because this type of doctor frequently changes from one hospitalist to another hospitalist on a daily basis. If a hospitalist administration team member makes the hospitalist's patient assignments, then the administrator can use the "Manage Patient's Care Team" page of the intranet App to update the hospitalist assignments. The intranet App automatically updates the patient's App and the provider's App, and possibly the App of a friend or family member, to reflect the changes made via the intranet App.

Referring to FIG. 14, another portion of the home screen generated by the intranet App is a list of the provider's (e.g., nurse, physical therapist, case manager, doctor) patients titled "My Patients" or "My Patients List." It is assumed that most doctors prefer to use the provider's App installed on their smart devices to interact with the patient's App due to the provider's App's simplicity and ease of use. In an embodiment, the other types (non-doctors) of providers who interact with the patient's App (e.g., nurses, social workers, physical therapists) use the intranet App instead of a mobile configuration of the App. This "My Patients" section lists all the patients who are assigned to the provider numerically by room number. In response to a nurse logging into an intranet App, the intranet App displays a list of the patients assigned to him/her. Throughout the day as assignments change, for example, because a new patient is admitted to the floor, the clerk or nurse can search for the patient via the "Manage Care Team" or "Manage Care Team Groups" page of the intranet App (see FIG. 39), and add the patient to the appropriate nurse's list of patients. Each floor clerk also can assign himself/herself a list of patients if he/she chooses to assist in entering data for the patient, such as Patient Location. Case managers and therapists also can view their own lists of patients under "My Patient List" (see FIG. 39) when they log into the intranet App. In response to the clerk, or another person, clicking on the patient's name on the clerk's, or other person's, list, the intranet App proceeds to generate another screen where the clerk, or other person, can manage information that is sent to the patient version of the App installed on the patient's smart phone.

Figure 36:
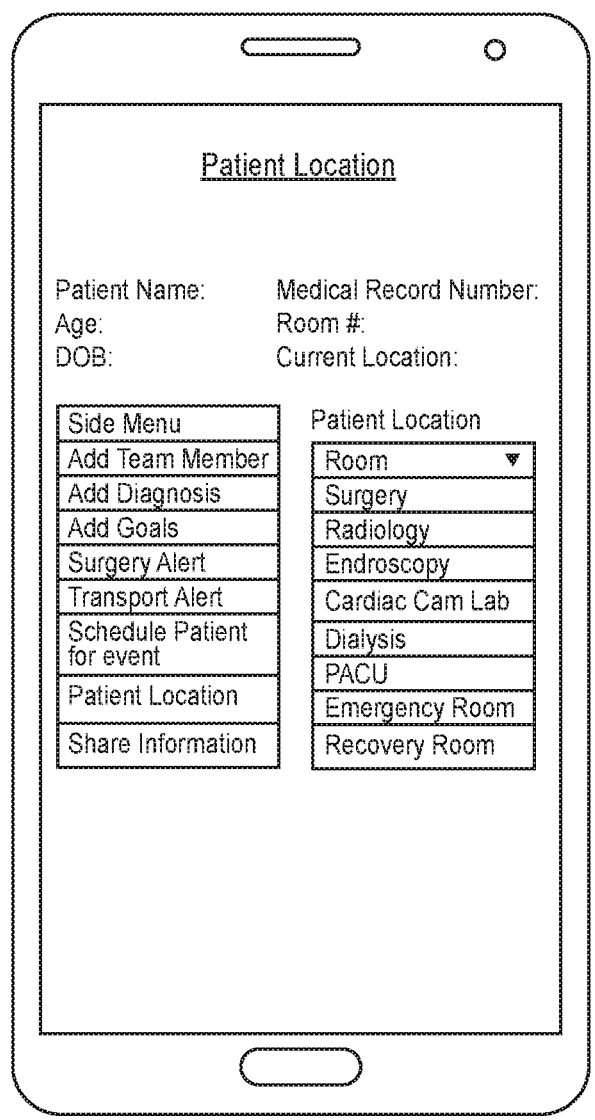
FIG. 36 is a screen view of an electronic device that is configured to execute one or more instructions of a medical-stay-related software application, and to display, in response to the executed one or more instructions, a patient's location and a menu via which a member of a patient's healthcare team can enter or update information about a patient's physical location during the patient's medical stay, according to an embodiment.
Figure 40:
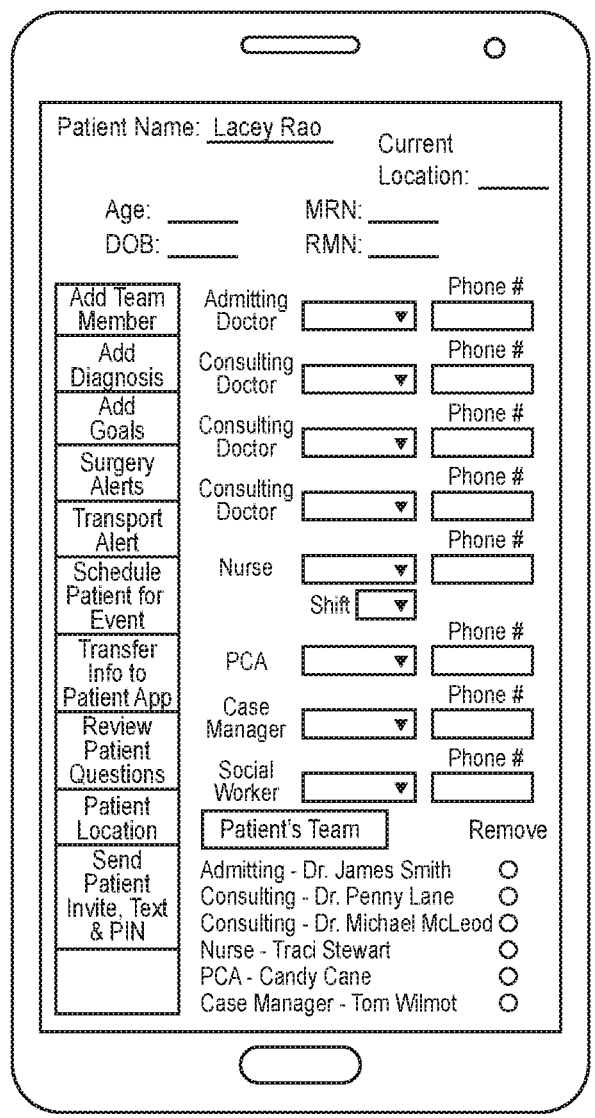
FIG. 40 is a screen view of an electronic device that is configured to execute one or more instructions of a medical-stay-related software application, and to display, in response to the executed one or more instructions, a page that provides, to a medical professional, information regarding a patient and that allows the medical professional to enter additional information regarding the entire medical team caring for the patient, according to an embodiment.

Referring to FIGS. 36 and 40, at, for example, the top of the Patient-Management screen (FIG. 40) is the patient's name, age, date of birth, room number, medical-record number, and current location; the intranet App "pulls" this information from the EMR (the device on which the intranet App is installed is configured for communication with the device on which is stored the EMR). On, for example, the left side of the screen is a side bar with different headings of information that appears in the patient's App, and, by clicking on the heading, the clerk, or other person, can update this information; the intranet App is configured to push this updated information to the patient's App and to family members' and friends' Apps (and also to providers' Apps).

Examples of headings to choose from on the side bar on the left include: Add a Provider or Team Member, Add Patient Goals, Surgery Alerts, Schedule Patient for an Event, Patient Location, Share Information, Transport Alert, and Add Diagnosis.

Under Add a Team Member, if a patient has a case manager, social worker, or physical therapist, for example, assigned to him/her, or the patient has any other provider who has not automatically been assigned to the patient via the EMR, the clerk or other person can add such provider to the My Care Team page (FIGS. 16-17) of a patient's App installed on the patient's smart device. The added information is also provided to the provider's App on the Patient's Care Team or Patient's Health Team page (FIG. 34).

On an Add Patient Goals page (FIG. 22) of the intranet App, one (most likely the patient's nurse) selects from a pick list of common patient goals, such as incentive spirometry, ambulate in halls 4 times a day, tolerate oral diet, up to chair, transition to oral pain meds, etc., which is displayed with a bubble next to the goal to allow one to select the goal for the patient. Whatever goals are selected are communicated from the intranet App to the patient App installed on the patient's smart device directly or via a communication network, and appear under (FIG. 21) the My Goals icon, such that the patient can view the desired goals for his/her day. Of course, these goals also can be modified by any of the patient's health care providers via the intranet App.

Referring to FIG. 40, under the Surgery Alerts tab, the intranet App is configured to display alerts for inpatient and outpatient surgery, which alerts can be managed by the nurse in the operating room with the patient, and to provide these alerts to the patient's App and the Apps of authorized family and friends. These alerts keep the patient's family and friends updated about the patient's progress in surgery via the family member's App and friends' App. After the surgical time out (time between surgery prep and the start of the surgery) is completed and the surgeon makes a first incision, the nurse in the operating room (OR) can send via the intranet App, for example, an alert "Surgery Has Started" to the Apps of authorized family and friends. This allows family members and friends in the waiting room to know when the surgical procedure has started. Once the Intranet App has issued the "Surgery Has Started" alert, the Intranet App automatically sends an alert that states "Surgery Still In Progress", e.g., hourly, until the operating-room nurse causes the Intranet App to broadcast another alert such as "Surgery Has Been Completed." Therefore, authorized family members and friends receive, via their respective Apps, another alert after the surgery is completed and the patient is in the recovery room. For example, the operating-room nurse sends, via the intranet App, an alert that states "Surgery has been completed and patient is proceeding to the recovery room." Furthermore, in response to the sending of a "Surgery has been completed . . . " alert, in all Apps (patient, provider, family member, friend, intranet) process and display a change in the patient's location from "Surgery" to "Recovery Room."

Referring to FIGS. 36 and 40, on the Schedule Patient For An Event page (accessed by pressing the displayed button "Schedule Patient for Event") of the intranet App, events such as Surgery, X-ray, CT Scan, Ultrasound, MRI, Dialysis, and procedures such as Cardiac Catheterization or Endoscopy are available for one to choose from. Once the surgery scheduler or radiology clerk or another employee schedules a patient for an event, he/she logs into the intranet App and inputs/selects the patient's event. The clerk first selects "Search for a Patient" (see FIG. 39) on the home screen of the intranet App. After selecting the patient's name, the intranet App takes the clerk to a Patient-Management screen (FIG. 40) for that patient, where the clerk can choose the icon "Schedule Patient for an Event." The intranet App displays a list of event types to choose from; once the type of event is chosen, the clerk enters the date and time, and then selects a "submit event" button to send the event information to the My Schedule page (FIG. 12) of the patient's App installed, e.g., on the patient's smart phone, and to the Patient's Schedule page of the one or more providers' Apps; the Patient's Schedule of a provider's App can be similar to the My Schedule page of the patient's App. The event then is displayed on the My Schedule and the Patient's Schedule pages in the patient's and the one or more providers' Apps, respectively.

On a Patient Location page (right side of FIG. 36) of the intranet App, the default location is "Room." In response to a patient leaving the room, or the floor, for surgery or an imaging study, or transport coming to collect the patient, a clerk updates the patient location to "Surgery" or "Imaging Study" via the intranet App. In response to the OR nurse hitting a "Surgery Completed" alert button on the intranet App, the intranet App changes the location of the patient to "Recovery Room." The intranet App broadcasts this information to the one or more providers' App(s) so that the doctor(s) know(s) if the patient is in his/her room or if the patient is in another location. The information is also broadcast to the patient App installed on the patient's smart device, and to the family-members' and friends' Apps respectively installed on the family members' and friends' smart devices; while the patient probably knows where he/she is, listing the location on all Apps allows the patient, family members, and friends to know the location of the patient (in his/her room or at another location) at virtually all times.

And on a Share Information page of the intranet App (the Share Information page is accessible, for example, under the Share Information button of FIG. 36), clicking on the Share Information button allows a provider, or other medical professional, to send information to the patient's App; examples of such information include links to websites or links to patient-information hand-outs. For example, if the patient has a case manager assigned to him/her and the patient is scheduled to go to a nursing home after his/her hospitalization, a social worker can send the patient links to websites of the nursing homes for which he/she qualifies, so the patient can better research his/her different options. If a social worker feels a patient would benefit from available hand-outs for things such as diabetes education, support groups, and community resources, the social worker can send, via the intranet App, these hand-outs electronically to the patient, family members, and friends via the patient's, family members', and friends' Apps. This information can be located on the My Care Team page (FIGS. 16-17) of the patient's, family members', and —friends' Apps under Social Worker. In another example, if a physical therapist wishes to make handouts with an exercise protocol available to the patient, the physical therapist could upload those handouts from his/her hospital computer hard drive onto the intranet App, which uploads the handouts to the patient's App, the patient would receive the physical therapist's exercise handouts via the My Care Team portion of the patient's App, and these documents would also be available to family members' and friends' Apps under on a page accessible via a displayed button "Physical Therapist."

Figure 42:
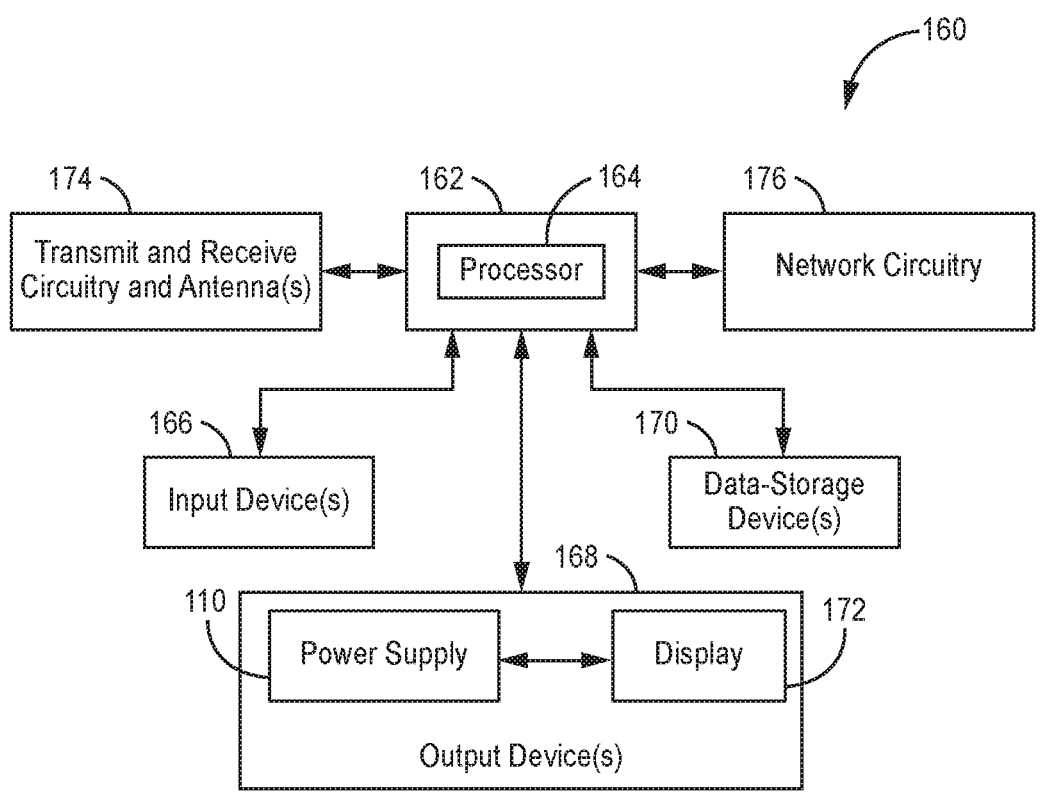
FIG. 42 is a circuit diagram of a device, such as a smart phone, that can load, install, and run a medical-stay-related software application, according to an embodiment.

FIG. 42 is a diagram of a system on which one or more of the above-described Apps can be disposed and can operate. The system includes one or more patient devices each configured to run, or execute, a respective patient App, one or more medical-professional devices (e.g., a physician's device, nurse's device, other caregiver's device) each configured to execute a respective medical-professional App (e.g., physician's App, nurse's App, other caregiver's App), one or more family/friend devices each configured to run a respective family-member or friend App, and one or more medical-facility devices (e.g., desktop computer) each configured to execute a respective medical-facility App (e.g., intranet App). For example, one or more of the devices each can be a respective smart phone, respective laptop computer, respective tablet computer, a respective desktop computer, or a respective other computing device. Each of the devices includes respective computing circuitry configured to run a respective App, a respective display device configured to display pages and other information generated by the respective App, a respective memory circuit or device configured to store the program code that constitutes the respective App, and respective communication circuitry configured to allow communications between the device and one or more other devices directly or via one or more communications networks (e.g., the cloud) and one or more databases. Examples of suitable communication networks include a cellular network, a wireless local-area network (LAN), and the internet. And examples of suitable databases include a hospital database. Alternatively, some or all of the devices can be configured to communicate with each other directly, for example, via a BlueTooth® wireless connection. For security, communications between any of the patient, medical professional, family-and-friend, and intranet Apps can be encrypted one or both ways. Furthermore, data stored onboard any of the devices or on the database can be encrypted for a further level of security.

FIG. 42 is a block diagram of an embodiment of a system or device 160, which is configured to download, to store, to install, and to run an embodiment of the above-described medical-stay-related software application, according to an embodiment. Examples of the device 160 include, but are not limited to, a smart phone, a pad computer, a tablet computer, a laptop computer, a personal computer, a local-server computer, and a cloud-server computer.

The device 160 includes computing circuitry 162, which includes a processor 164; the device also includes at least one input device 166, at least one output device 168, at least one data-storage device 170, at least one transmit-and-receive circuitry 174 including at least one antenna, and network circuitry 176.

The at least one output device 168 includes a display 172 and a power supply 110, which powers the display. For example, the display 172 may be a liquid-crystal display (LCD) for a smart phone. Although not shown in FIG. 42, the device 160 can include one or more additional power supplies to power components and circuits of the device other than the display 172, or the power supply 110 can be configured to power the other components and circuits in addition to the display.

The processor 164 can be, for example, a microprocessor or microcontroller, and is configured to execute program instructions that form, or that are otherwise part of, the medical-stay-related software application (also referred to herein as "the App"). For example, while executing, and in response to, the App's program instructions, the processor 164 is configured to perform, and does perform, some or all of the above-described functions and operations attributed to the medical-stay-related software application either alone or in cooperation with other circuitry and components of the device 160.

The input device (e.g., a displayed or physical keypad or keyboard, a voice-command component, a mouse) 166 allows the providing of data, programming, and commands to the computing circuitry 162.

The display 172 (and any other included output device 168) allows the computing circuitry 162 to provide data in a form (e.g., still image, video, menu, web or other page such as a data-entry or data-display page) perceivable by a human operator such as a patient, a medical professional, a member of the patient's family, another relative of the patient, and a friend of the patient. In an embodiment, the display 172 is a touch screen configured to allow a user to select an icon (see, e.g., FIG. 4) or another item displayed on the screen by touching a portion of the screen over the displayed icon or other item.

The data-storage device (e.g., hard-disk drive, optical drive, and solid-state memory such as a flash drive, RAM, EPROM, and EEPROM) 170 allows for the storage of, e.g., programs and data such as an embodiment of the above-described medical-stay-related software and data acquired by, generated by, and otherwise related to the medical-stay-related software application.

The transmit and receive circuitry 174 (also called a transceiver) includes one or more antennas, and is configured to transmit data from the device 160 to one or more remote devices (e.g., a hospital server on which resides a hospital database that stores information about patients staying at the hospital) or other remote destinations, and to receive data from one or more remote devices (e.g., the aforementioned hospital server) or other remote sources. The transmit and receive circuitry 174 is configured to communicate with one or more such remote devices using one or more suitable protocols such as a cellular-network protocol (e.g., 4G, 5G), Bluetooth®, and WiFi®, and may include a respective antenna for each protocol for which the device 160 is configured. For example, in an embodiment the device 160 is configured to download the medical-stay-related software application, and to transmit and to receive data related to the medical-stay-related software application, via the transmit and receive circuitry 174.

Figure 43:
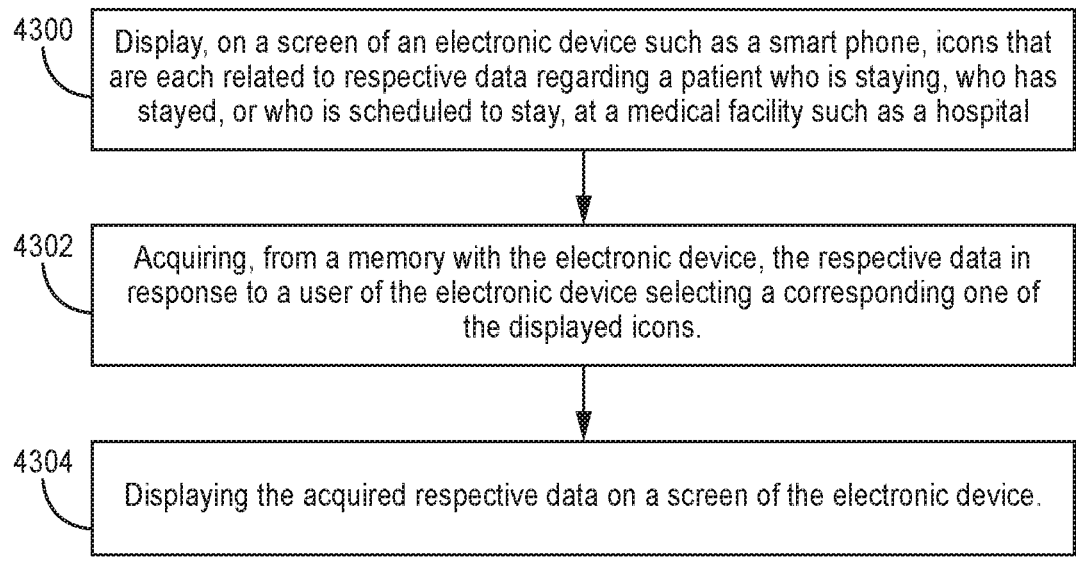
FIG. 43 is a flow diagram of the operation of the device of FIG. 42 while executing a medical-stay-related software application, according to an embodiment.

And the network circuitry 176 is configured to allow the device 160 to communicate with remote devices over one or more networks, such as a cellular network and a local-area network (LAN). For example, in an embodiment, the network circuitry 176 includes an input port (e.g., a USB port) that is configured to allow the computing circuitry 162 and other components of the device 160 to communicate with another device over a conductive cable such as an Ethernet cable. Or the network circuitry 176 can cooperate with the transmit and receive circuitry 174 to allow the computing circuitry 162 and other components of the device 160 to communicate with one or more other devices over a wireless channel. For example, in an embodiment the device 160 is configured to download the medical-stay-related software application, and to transmit and to receive data related to the medical-stay-related software application, via the network circuitry 176 and the transmit and receive circuitry 174. FIG. 43 is a flow diagram of the operation of the device 160 of FIG. 42 while executing the medical-stay-related software application (the App), according to an embodiment.

Referring to FIGS. 42 and 43, at a step 4300, the electronic device 160 displays, on the touch display screen 172, icons that are each related to respective data regarding a patient who is staying, who has stayed, or who is scheduled to stay, at a medical facility such as a hospital. The electronic device 160 displays the icons upon starting/opening the App (subsequent to the initial starting/opening of the App after its installation), for example, in response to a user "touching" an App icon on the display screen 172. Further in example, referring to FIG. 4, the electronic device 160 is a smart phone that displays, on the display screen 172, twelve icons each related to respective data including, but not limited to, a list of the doctors on the patient's healthcare team (icon My Doctors), information about the medical facility (icon My Hospital), instructions and prompts for inviting family and friends to download and install the App on their electronic devices (e.g., from a hospital website or from application providers such as Google Play and the Apple Store) and authorizing them to view some or all of the data to which the App has access regarding the patient (icon Invite Family & Friends), and the patient's calendar/schedule during, and even after (e.g., for follow-up medical appointments), his/her stay (icon My Schedule).

Figure 41:
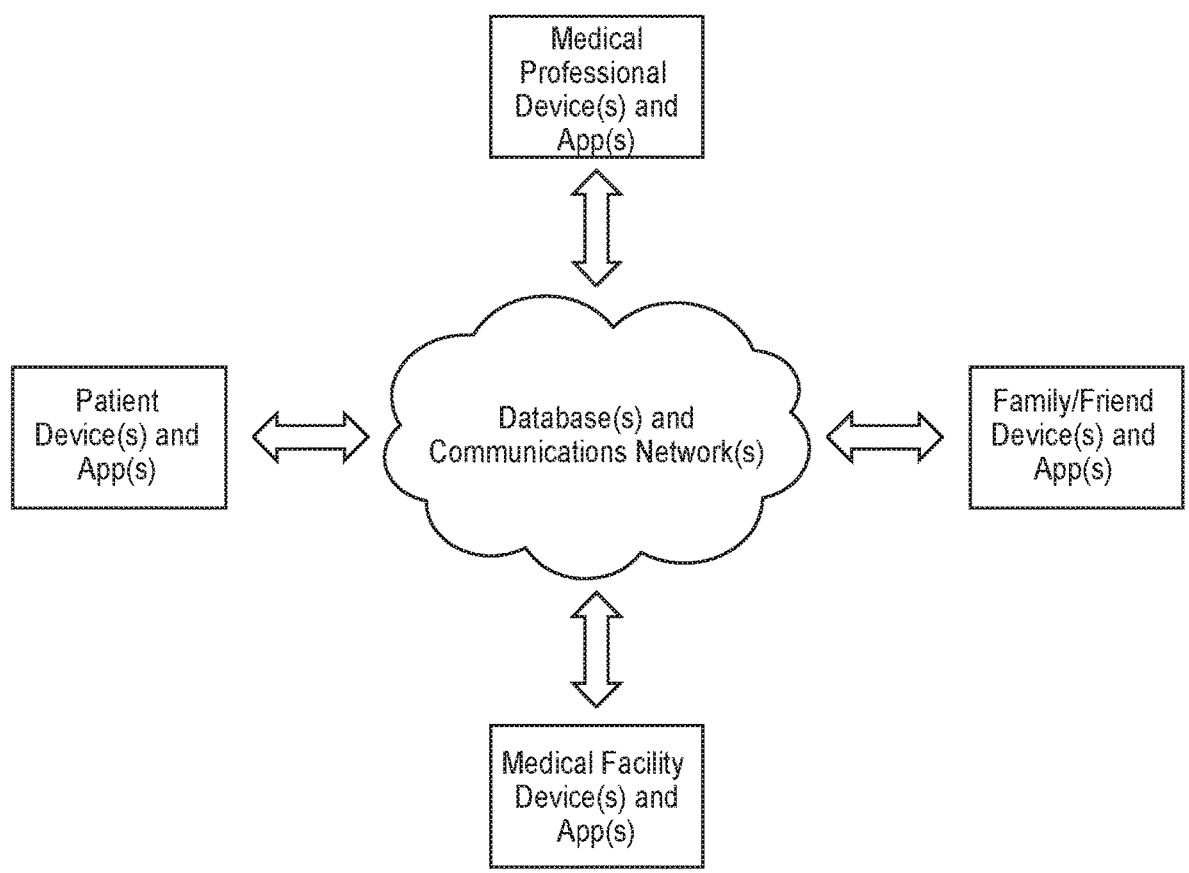
FIG. 41 is a diagram of a system that includes a number of devices each configured to execute one or more instructions of a medical-stay-related software application, a database of patient information, and a network via which the devices can communicate with each other and with the database, according to an embodiment.

Next, at a step 4302, in response to a user selecting one of the information icons displayed on the screen 172, for example, by touching the portion of the screen over the selected icon, the processor 164 acquires, from a memory, the respective data corresponding to the selected icon. For example, referring to FIG. 4, if a user "touches" the icon My Care Team, then the processor 164 acquires, or otherwise retrieves, from a memory, a list of the medical professionals on the patient's care team. If the electronic device 160 already has downloaded the list from a database (FIG. 41), such as a hospital database, and already has stored the list in a local memory that is part of the data-storage device(s) 170, then the processor 164 acquires, or otherwise retrieves, the list from the local memory. If, however, the list has not already been downloaded, then the processor 164 acquires, or otherwise retrieves, the list from a database, such as a hospital database, via the transmit and receive circuitry and antenna(s) 174 and possibly via the network circuitry 176 (the App instructions/code includes the information needed for the processor to identify, to communicate with, and to be granted access to, the database). After downloading the list, the processor 164 stores the list in local memory that is part of the data-storage device(s) 170. If the retrieved data is encrypted, then the processor 164 can store the data (in local memory) in its decrypted form, decrypt the data and store the data (in local memory) in an unencrypted form, or decrypt the data, re-encrypt the data, and store the data (in local memory) in re-encrypted form.

Then, at a step 4304, the processor 164 displays the acquired, or otherwise retrieved, data on the display screen 172. Further to the above example, if the data is a list of medical professionals on a patient's care team, then the processor 164 retrieves the list from local memory 170 and causes the display screen 172 to display the list. If the list is stored in local memory 170 in encrypted form, then the processor 164 decrypts the list before causing the display screen to display the list.

After displaying the data on the display screen 172, the processor 164 can retain the data in local memory 170 in encrypted or unencrypted form, or can delete the data such that the data is only temporarily stored on the electronic device 160 while a user is viewing the data.

Figure 44:
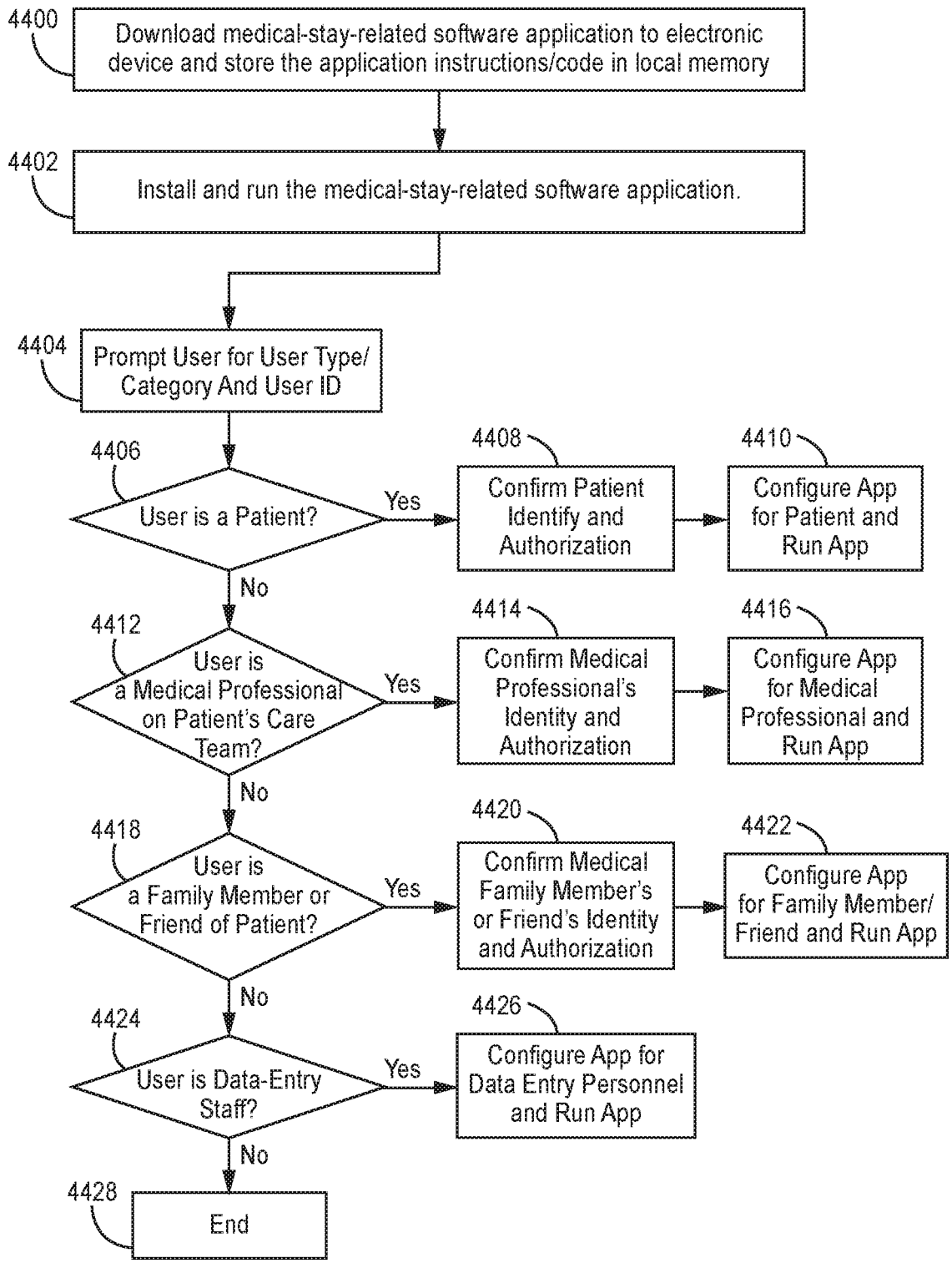
FIG. 44 is a flow diagram of a procedure by which the device of FIG. 42 downloads, installs, configures, and runs a medical-stay-related software application, according to an embodiment.

FIG. 44 is a flow diagram of the operation of the device 160 of FIG. 42 while executing the medical-stay-related software application (the App), according to another embodiment.

Referring to FIGS. 42 and 44, at a step 4400, the processor 164 downloads the medical-stay-related software application (the App) via the transmit and receive circuitry 174 (possibly in cooperation with the network circuitry 176), and stores the App (e.g., the instructions/code that forms the App) in a memory 170 (although not shown in FIG. 42, the data storage device(s) 170 can be coupled to the transmit and receive circuitry 174 or the network circuitry 176 without using the computing circuitry 162 as an interface). The processor 164 can download the App from any suitable location such as a hospital website, Google Play®, or the Apple Store®)

Next, at a step 4402, the processor 164 installs the downloaded App, and, at the request of a user (e.g., a patient) of the device 160, runs the App.

Then, at a step 4404, because this is the first time that the processor 164 is running the App after its installation on the device 160, the processor, via the display 172, prompts the user for information as to the user's category (e.g., patient, medical professional, patient friend, patient family member) and the user's identity.

If, at a step 4406, the processor 164 determines that the user is a patient, then the processor requests, via the transmit and receive circuitry 174 (and possibly the network circuit 176) from a remote source, e.g., a database of a hospital at which the patient is staying, confirmation of the patient's identity and his/her authorization to use the App to access his/her medical-stay-related information.

Next, at a step 4408, in response to receiving, from the queried remote source, confirmation that the patient is who he/she represents and that the patient has authorization to use the App to access his/her medical-stay-related information, the processor 164, at a step 4410, configures the App for a patient, runs the patient-configured App, and, in response to executing the programming instructions of the patient-configured App, performs tasks in response to requests from the patient, such requests including to view a particular page generated by the App, submits patient questions to a member of the patient's healthcare team, and, in response to an authorization request from a third party such as a family member or friend of the patient, authorizes the requestor to view, via the requestor's version of the App, patient-selected information related to the medical stay of the patient.

If, at a step 4412, the processor 164 determines that the user is a medical professional, such as a doctor, on a patient's medical care team, then the processor requests, via the transmit and receive circuitry 174 (and possibly the network circuit 176) from a remote source, e.g., a database of a hospital at which the patient is staying, confirmation of the medical professional's identity and his/her authorization to use the App to access information regarding the patient.

Then, at a step 4416, in response to receiving, from the queried remote source, confirmation that the medical professional is who he/she represents and has authorization to use the App to access the patient's medical-stay-related information, the processor 164, at a step 4416, configures the App for a medical professional, runs the configured App, and in response to executing the programming instructions of the medical-professional-configured App, performs tasks of the configured App including servicing requests from the medical professional, such requests including to view a particular page generated by the App, to answer questions submitted by the patient via the patient's App, to update information (e.g., that a patient is out of surgery), and to send alerts (e.g., the doctor will be seeing the patient in 20 minutes) to the patient and his/her family members and friends.

If, at a step 4418, the processor 164 determines that the user is a family member or friend of the patient, then the processor requests that the user enter, via a confirmation page that the processor generates on the display 172, a confirmation number, or other value, and confirms that the confirmation number is valid by contacting, via the transmit and receive circuitry 174 (and possibly the network circuit 176) a database of a hospital at which the patient is staying, or the patient's device that runs the patient's version of the App and through which the confirmation number, if valid, was generated. For example, the patient's device, in response to executing the patient's App, generates a code and sends the code (e.g., via text, email, or voice) to the family member's or friend's device, and the family member or friend manually enters the confirmation code via the confirmation page that the App displays on the family member's or friend's device.

Next, at a step 4420, in response to receiving confirmation that the family member or friend entered a valid code and is, therefore, authorized, at a step 4422 the processor 164 configures the App for a family member/friend, runs the so-configured App, and in response to executing the programming instructions of the family-member-friend-configured App, performs tasks in response to requests from the family member or friend, such requests including to view a particular page generated by the App such as the patient's schedule or a page indicating when a patient will be out of surgery, and to submit questions to one or more members of the patient's medical care team.

If, at a step 4424, the processor 164 determines that the user is data-entry staff or personnel tasked with entering data into the database of the hospital at which the patient stayed/is staying/is scheduled to stay and updating the information displayed by the Apps of the patient, medical professionals on the patient's care team, and family and friends of the patient, and, assuming that the processor is part of the hospital's computer system, the processor grants access to the user under the assumption that if the user is accessing the hospital's computer system, then he/she has the authority to do so and to use the App.

Then, at a step 4426, the processor 164 configures the App for a data-entry staff and intranet/database use, runs the so-configured App, and in response to executing the App, performs operations of the App such as updating information (e.g., patient's schedule, list of members of the patient's care team) regarding the patient and broadcasting the updated information to other devices running the App for other App users such as the patient, medical professionals on the patient's healthcare team, and family and friends of the patient.

And if at the step 4424 the processor 164 determines that the user is not a patient, medical professional on the patient's care team, a family member or friend, or a member of the data-entry staff, then, at a step 4428, the processor closes the App; alternatively, the processor can return to step 4404 from step 4424.

Referring to FIGS. 1-44, alternate embodiments of the above-described medical-stay-related software application, a device 160 that is configured to execute the software application, and a network over which the devices communicate with each other and with a database, are contemplated. For example, an embodiment described for one portion of the App, device 160, or network may be applicable to another portion of the App, device 160, or network. Furthermore, a person can be both a member of the patient's care team and data-entry personnel.

In summary, the above-described App can have at least four configurations: a patient configuration, a healthcare-professional configuration, a family-friend configuration, and a data-entry/intranet configuration. The device executing the App can configure the App in one of the aforementioned configurations in response to information provided by a user, indicating, for example, that he/she is a patient, a doctor, a family member or friend, or medical staff. The App can be configured to check with, for example, a hospital database to confirm that a requestor is actually a patient, or a member of the medical staff, at the hospital. Furthermore, the App can provide security by encrypting data that is stored on the device on which the App is running, and also encrypting communications between devices running the App and other such devices and the hospital database(s). Moreover, the App can provide security by reducing or eliminating granting access to a patient's medical information to a person falsely claiming to be a family member, a friend, or another person close to the patient. In addition, any configuration of the App can run in the background, but still can generate an alarm or other notification in response to an alert (e.g., a scheduled alarm) from the App itself or from another App (e.g., an unscheduled alarm) while running in the background.

From the foregoing, it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. Moreover, circuit components described above may be disposed on a single or multiple IC dies to form one or more ICs, these one or more ICs may be coupled to one or more other ICs. In addition, any described component or operation may be implemented/performed in hardware, software, firmware, or a combination of any two or more of hardware, software, and firmware. Furthermore, one or more components of a described apparatus or system may have been omitted from the description for clarity or another reason. Moreover, one or more components of a described apparatus or system that have been included in the description may be omitted from the apparatus or system.

The invention claimed is:

1. A tangible, non-transitory computer-readable medium storing instructions that, when executed by a first computing circuit, cause the first computing circuit, or a circuit or device coupled to or including the first computing circuit:
   to be configured in one of a patient configuration, a medical-professional configuration, and a friends-and-family configuration;
   to display icons that correspond to the configuration and that are each related to respective data regarding a patient at a medical facility;
   to acquire, from a memory, the respective data in response to a user selecting a related one of the displayed icons;
   to display the acquired respective data; and
   while configured in the medical-professional configuration, to send, in response to a user selecting, from the displayed data, the patient and a send item that is associated with a rounding delay, a rounding alert that includes the rounding delay to a second computing circuit remote from the first computing circuit and configured in one of a patient configuration and a friends-and-family configuration.

2. The tangible non-transitory computer-readable medium of claim 1 wherein one of the icons is related to data regarding a medical professional on the patient's care team.

3. The tangible non-transitory computer-readable medium of claim 1, wherein one of the icons is related to data regarding the patient's medical history.

4. The tangible non-transitory computer-readable medium of claim 1, wherein one of the icons is related to data regarding the patient's schedule while staying at a medical facility.

5. The tangible non-transitory computer-readable medium of claim 1, wherein one of the icons is related to data regarding the patient's location while staying at a medical facility.

6. The tangible, non-transitory computer-readable medium of claim 1 storing instructions that, when executed by a computing circuit, cause the computing circuit, or a circuit or device coupled to or including the computing circuit:
   to receive an authorization code from a remote device; and
   in response to the authorization code, to grant the remote device access to the respective data represented by one or more of the icons.

7. The tangible, non-transitory computer-readable medium of claim 1 storing instructions that, when executed by a computing circuit, cause the computing circuit, or a circuit or device coupled to or including the computing circuit:
   to receive an authorization code from an input device;
   to send the authorization code to a remote device; and
   to receive from the remote device authorization to access the respective data represented by one or more of the icons.

8. The tangible, non-transitory computer-readable medium of claim 1 storing instructions that, when executed by a computing circuit, cause the computing circuit, or a circuit or device coupled to or including the computing circuit:
   to receive an authorization code from a remote device;
   to receive, from an input device, an identification of the data for which access can be granted to the remote device; and
   in response to the authorization code, to grant the remote device access to the identified data respectively represented by one or more of the icons.

9. The tangible, non-transitory computer-readable medium of claim 1 storing instructions that, when executed by a computing circuit, cause the computing circuit, or a circuit or device coupled to or including the computing circuit to send, to a remote device, an invitation to request access to the respective data represented by one or more of the icons.

10. The tangible, non-transitory computer-readable medium of claim 1 storing instructions that, when executed by a computing circuit, cause the computing circuit, or a circuit or device coupled to or including the computing circuit:
    to receive, via an input device, data represented by one of the icons; and
    to broadcast the received data to a remote device that is authorized to receive the data.

11. The tangible, non-transitory computer-readable medium of claim 1 storing instructions that, when executed by a computing circuit, cause the computing circuit, or a circuit or device coupled to or including the computing circuit:
    to receive, via an input device, a change to data represented by one of the icons; and
    to broadcast the change to a remote device that is authorized to receive the data.

12. The tangible, non-transitory computer-readable medium of claim 1 storing instructions that, when executed by a computing circuit, cause the computing circuit, or a circuit or device coupled to or including the computing circuit:
    to encrypt the data represented by one or more of the icons; and
    to store the encrypted data in a memory.

13. A method, comprising:
    displaying, with a first electronic device having a medical-professional configuration, a set of icons, the set corresponding to the medical-professional configuration, each of the icons related to respective data regarding a patient at a medical facility;
    acquiring, from a memory with the first electronic device, respective data in response to a user selecting a related one of the displayed icons;
    displaying the acquired respective data; and
    sending, in response to the user selecting, from the displayed data, the patient and a send item that is associated with a rounding delay, a rounding alert to a second electronic device remote from the first electronic device and having one of a patient configuration and a friends-and-family configuration.

14. The method of claim 13 wherein the memory forms part of the first electronic device.

15. The method of claim 13 wherein the memory forms part of a remote device.

16. The method of claim 13, further comprising:
    receiving, from the second electronic device, a question from a user of the second electronic device;
    displaying, with the first electronic device, the question;
    receiving, with the first electronic device, an answer to the question from the user of the first electronic device; and
    sending the answer to the second electronic device.

17. The method of claim 13, further comprising:
    displaying, with the first electronic device, a question received from the second electronic device in response to the user of the first electronic device selecting a corresponding one of the displayed icons;
receiving from the user of the first electronic device via an input device that is coupled to, or that forms part of, the first electronic device, an answer to the question; and
sending the answer to the second electronic device.

18. The method of claim 13, further comprising:
receiving with the first electronic device, from a remote database for each of the icons, the respective data;
storing the received respective data in the memory, which forms part of the first electronic device; and
wherein the acquiring includes acquiring, from the memory with the first electronic device, the respective data in response to a user of the first electronic device selecting a corresponding one of the displayed icons.

19. The method of claim 13 wherein the memory is remote from the first electronic device.

20. An electronic device, comprising:
a display screen;
a memory circuit; and
computing circuitry coupled to the display screen and to the memory circuit and configurable
in one of a patient configuration, medical-professional configuration, and a friends-and-family configuration;
to cause the display screen to display icons that correspond to the configuration of the computing circuitry and that are each related to respective data regarding a patient at a medical facility,
to retrieve, from the memory, the respective data in response to a user of the electronic device selecting, via the display screen, a related one of the displayed icons; and
to cause the display screen to display the retrieved respective data; and
while configured in the medical-professional configuration, to send, in response to a user selecting, from the displayed data, the patient and a send-alert item that is associated with a rounding delay, a rounding alert to a remote device having other computing circuitry configured in one of a patient configuration and a friends-and-family configuration.

21. The electronic device of claim 20 wherein the computing circuitry is configured:
to receive an authorization code from a remote device; and
in response to the authorization code, to grant the remote device access to the respective data represented by one or more of the icons.

22. The electronic device of claim 20, further comprising:
a data-input device; and
wherein the computing circuitry is configured:
to receive an authorization code from the data-input device;
to send the authorization code to a remote device; and
to receive from the remote device authorization to access the respective data represented by one or more of the icons.

23. The electronic device of claim 20 wherein the display screen includes the data-input device.

24. The electronic device of claim 20, further comprising:
a data-input device; and
wherein the computing circuitry is configured
to receive an authorization code from a remote device,
to receive, from the data-input device, an identification of the data for which access can be granted to the remote device, and
in response to the authorization code, to grant the remote device access to the identified data respectively represented by one or more of the icons.

25. The electronic device of claim 20 wherein the computing circuit is configured to send, to a remote device, an invitation to request access to the respective data represented by one or more of the icons.

26. The electronic device of claim 20, further comprising:
a data-input device; and
wherein the computing circuit is configured:
to receive, via the data-input device, data represented by one of the icons; and
to broadcast the received data to a remote device that is authorized to receive the data.

27. The electronic device of claim 20, further comprising:
a data-input device; and
wherein the computing circuit is configured:
to receive, via the data-input device, an update to data represented by one of the icons; and
to broadcast the update to a remote device that is authorized to receive the data.

28. The electronic device of claim 20 wherein the computing circuit is configured:
to encrypt the data represented by one or more of the icons; and
to store the encrypted data in the memory circuit.

29. The method of claim 13 wherein the sending includes sending the rounding alert in response to the user selecting, from the displayed data, the rounding delay.

30. The electronic device of claim 20 wherein the computing circuitry is configurable to send the rounding alert in response to the user selecting, from the displayed data, the rounding delay.

31. The tangible, non-transitory computer-readable medium of claim 1 wherein the displayed data includes the rounding delay.

32. The method of claim 13 wherein the rounding delay is an estimate of a time between the sending of the rounding alert and a medical professional seeing the patient.

33. The method of claim 13 wherein the rounding delay is an estimate of a time between the sending of the rounding alert and the user seeing the patient.

34. The method of claim 13 wherein sending the rounding alert includes sending the rounding alert in response to the user selecting the rounding delay from the displayed data.

35. The electronic device of claim 20 wherein the rounding delay is an estimate of a time of a medical professional seeing the patient.

36. The electronic device of claim 20 wherein the rounding delay is an estimate of a time of the user seeing the patient.

37. The electronic device of claim 20 wherein the computing circuit is configured to send the rounding alert in response to the user selecting the rounding delay from the displayed data.

* * * * *